United States Patent [19]
Weissbach et al.

[11] Patent Number: 5,639,651
[45] Date of Patent: Jun. 17, 1997

[54] GAP-RELATED GENE, HUMAN IQGAP1

[75] Inventors: Lawrence Weissbach, Boston; Andre Bernards, Lexington; Jeffrey Settleman, Boston, all of Mass.

[73] Assignee: The General Hospital Corporation, Boston, Mass.

[21] Appl. No.: 287,959

[22] Filed: Aug. 9, 1994

[51] Int. Cl.$^6$ .............. C12N 15/12; C12N 15/85
[52] U.S. Cl. .............. 435/325; 435/252.3; 435/348; 536/23.5; 530/350
[58] Field of Search .............. 536/23.2, 23.5; 435/252.3, 193, 227, 240.1, 240.2, 240.4; 530/350

[56] References Cited

FOREIGN PATENT DOCUMENTS 9320201 10/1993 WIPO.

OTHER PUBLICATIONS

Gold, et al., *J. Immun.*, 150(2): 377–386, Jan. 15, 1993.
Lathe et al., *J. Mol. Biol.*, vol. 183, pp. 1–12, 1985.
Sambrook et al., *Molecular Cloning: A Laboratory Manual*, Cold Spring Harbor Press, 1989, pp. 11.3–11.19.
Barbacid, "ras Genes", 1987, *Am. Rev. Biochem.*, 56:779–827.
Basu, et al., "Aberrant Regulation of ras Proteins in Malignant Tumour Cells From Type 1 Neurofibromatosis Patients", 1992, *Nature*, 356:713–715.
Bourne, et al., "The GTPase Superfamily: Conserved Structure and Molecular Mechanism", 1991, *Nature*, 349:117–127.
Cheney, et al., "Unconventional Myosins", 1992, *Current Opin. in Cell Biology*, 4(1):27–35.
DeClue, et al., "Abnormal Regulation of Mammalian p21$^{ras}$ Contributes to Malignant Tumor Growth in von Recklinghausen (Type 1) Neurofibromatosis", 1992, *Cell*, 69:265–273.
Hall, "ras and GAP–Who's Controlling Whom?", 1990, *Cell*, 61:921–923.
Hall, "Signal Transduction through Small GTPases–A Tale of Two GAPs", 1992, *Cell*, 69:389–391.
Imai, et al., "Identificaiton of a GTPase–Activating Protein Homolog in Schizosaccharomyces Pombe", 1991, *Molecular and Cellular Biology*, 11:3088–3094.
Li et al., "Somatic Mutations in the Neurofibromatosis 1 Gene in Human Tumors", 1992, *Cell*, 69:275–281.
Liotta, et al., "Cancer Metastasis and Angiogenesis: An Imbalance of Positive and Negative Regulation", 1991, *Cell*, 64:327–336.
Martin, et al., "The GAP–Related Domain of the Neurofibromatosis Type 1 Gene Product Interacts with ras p21", 1990, *Cell*, 63:843–849.
Marx, "New Genes May Shed Light On Cell Growth Control", 1992, *Science*, 257:484–485.
Moran et al., "Src Homology Region 2 Domains Direct Protein–Protein Interactions in Signal Transduction", 1990, *Proc. Natl. Acad. Sci. USA*, 87:8622–8626.
Moscatelli, et al., "Membrane and Matrix Localization of Proteinases: a Common Theme in Tumor Cell Invasion and Angiogenesis", 1988, *Biochimica et Biophysica Acta*, 948:67–85.
Satoh, et al., "Function of Ras as a Molecular Switch in Signal Transduction", 1992, *J. Biol. Chem.*, 267:24149–24152.
Settleman, et al., "Association Between GTPase Activators for Rho and Ras Families", 1992, *Nature*, 359:153–154.
Settleman, et al., "Molecular Cloning of cDNAs Encoding the GAP–Associated Protein p190: Implications for a Signaling Pathway from Ras to the Nucleus", 1992, *Cell*, 69:539–549.
Tanaka, et al., "S. Cerevisiae Genes IRA1 and IRA2 Encode Proteins That May Be Functionally Equivalent to Mammalian ras GTPase Activating Protein", 1990, *Cell*, 60:803–807.
Trahey et al., "A Cytoplasmic Protein Stimulates Normal N–ras p21 GTPase, but Does Not Affect Oncogenic Mutants", 1987, *Science*, 238:542–545.
Vogel, et al., "Cloning of Bovine GAP and its Interaction with Oncogenic ras p21", 1988, *Nature*, 335:90–93.
Wang, et al., "Sar1, a Gene from Schizosaccharomyces Pombe Encoding a Protein that Regulates ras1", 1991, *Cell Regulation*, 2:453–465.
Weissbach, et al., "A Plasminogen–Related Gene is Expressed in Cancer Cells", 1992, *Biochemical and Biophysical Research Communications*, 186:1108–1114.
Yatani, et al., "ras p21 and GAP Inhibit Coupling of Muscarinic Receptors to Atrial k$^{3o}$ Channels", 1990, *Cell*, 61:769–776.

*Primary Examiner*—Dian C. Jacobson
*Assistant Examiner*—Keith D. Hendricks
*Attorney, Agent, or Firm*—Fish & Richardson P.C.

[57] ABSTRACT

A purified nucleic acid encoding the IQGAP1 protein, a novel member of the GTPase activating protein family, useful in the diagnosis and treatment of tumors.

8 Claims, 10 Drawing Sheets

| | | | | | |
|---|---|---|---|---|---|
| GGTATTAAAA | CTGATCTTTT | GACATTTTTG | ACAATGTTCT | TATAAATTAC | TTTCTTTTTT | 60
| ATCATATATG | GATGGGATGA | AGCACAGAGT | AAGATAGAGT | GCACAGCAAA | GGGGATCTGC | 120
| CCCTCCTATC | TGTCCAATAC | CCCACAGGTT | TTGGTGATAA | TCTTGGGCAA | TGTTCCAGTC | 180
| AAACCTGCCT | CCCACTTCTC | ACTAAAGTTA | GTGAACATGT | GACCCACATT | CCCCAAATAA | 240
| GAGCCTCTTA | TAAACTCCAT | TCTTGGCTTT | TTCATTCATA | GAGATAGCTA | TTTTATGAGA | 300
| CATAGATAAA | GCATTTTTTA | GTGATGTGCA | CGATGCCTTT | TTTCTTAATT | ATTAACTTCT | 360
| CAAAACATAA | ACACATTGGA | GGCACTTAAT | AAAGGGAGCT | GTACGTACCG | CCGTCCGCGC | 420
| CTCCAAGGTT | TCACGGCTTC | CTCAGCAGAG | ACTCGGGCTC | GTCCGCCATG | TCCGCCGCAG | 480
| ACGAGGTTGA | CGGGCTGGGC | GTGGCCCGGC | CGCACTATGG | CTCTGTCCTG | GATAATGAAA | 540
| GACTTACTGC | AGAGGAGATG | GATGAAAGGA | GACGTCAGAA | CGTGGCTTAT | GAGTACCTTT | 600
| GTCATTTGGA | AGAAGCGAAG | AGGTGGATGG | AAGCATGCCT | AGGGGAAGAT | CTGCCTCCCA | 660
| CCACAGAACT | GGAGGAGGGG | CTTAGGAATG | GGGTCTACCT | TGCCAAACTG | GGGAACTTCT | 720
| TCTCTCCCAA | AGTAGTGTCC | CTGAAAAAAA | TCTATGATCG | AGAACAGACC | AGATACAAGG | 780
| CGACTGGCCT | CCACTTTAGA | CACACTGATA | ATGTGATTCA | GTGGTTGAAT | GCCATGGATG | 840
| AGATTGGATT | GCCTAAGATT | TTTTACCCAG | AAACTACAGA | TATCTATGAT | CGAAAGAACA | 900
| TGCCAAGATG | TATCTACTGT | ATCCATGCAC | TCAGTTTGTA | CCTGTTCAAG | CTAGGCCTGG | 960
| CCCCTCAGAT | TCAAGACCTA | TATGGAAAGG | TTGACTTCAC | AGAAGAAGAA | ATCAACAACA | 1020
| TGAAGACTGA | GTTGGAGAAG | TATGGCATCC | AGATGCCTGC | CTTTAGCAAG | ATTGGGGGCA | 1080
| TCTTGGCTAA | TGAACTGTCA | GTGGATGAAG | CCGCATTACA | TGCTGCTGTT | ATTGCTATTA | 1140
| ATGAAGCTAT | TGACCGTAGA | ATTCCAGCCG | ACACATTTGC | AGCTTTGAAA | AATCCGAATG | 1200
| CCATGCTTGT | AAATCTTGAA | GAGCCCTTGG | CATCCACTTA | CCAGGATATA | CTTTACCAGG | 1260
| CTAAGCAGGA | CAAAATGACA | AATGCTAAAA | ACAGGACAGA | AAACTCAGAG | AGAGAAAGAG | 1320
| ATGTTTATGA | GGAGCTGCTC | ACGCAAGCTG | AAATTCAAGG | CAATATAAAC | AAAGTCAATA | 1380
| CATTTTCTGC | ATTAGCAAAT | ATCGACCTGG | CTTTAGAACA | AGGAGATGCA | CTGGCCTTGT | 1440
| TCAGGGCTCT | GCAGTCACCA | GCCCTGGGGC | TTCGAGGACT | GCAGCAACAG | AATAGCGACT | 1500
| GGTACTTGAA | GCAGCTCCTG | AGTGATAAAC | AGCAGAAGAG | ACAGAGTGGT | CAGACTGACC | 1560

FIG. 1A

```
CCCTGCAGAA GGAGGAGCTG CAGTCTGGAG TGGATGCTGC AAACAGTGCT GCCCAGCAAT    1620
ATCAGAGAAG ATTGGCAGCA GTAGCACTGA TTAATGCTGC AATCCAGAAG GGTGTTGCTG    1680
AGAAGACTGT TTTGGAACTG ATGAATCCCG AAGCCCAGCT GCCCCAGGTG TATCCATTTG    1740
CCGCCGATCT CTATCAGAAG GAGCTGGCTA CCCTGCAGCG ACAAAGTCCT GAACATAATC    1800
TCACCCACCC AGAGCTCTCT GTCGCAGTGG AGATGTTGTC ATCGGTGGCC CTGATCAACA    1860
GGGCATTGGA ATCAGGAGAT GTGAATACAG TGTGGAAGCA ATTGAGCAGT TCAGTTACTG    1920
GTCTTACCAA TATTGAGGAA GAAAACTGTC AGAGGTATCT CGATGAGTTG ATGAAACTGA    1980
AGGCTCAGGC ACATGCAGAG AATAATGAAT TCATTACATG GAATGATATC CAAGCTTGCG    2040
TGGACCATGT GAACCTGGTG GTGCAAGAGG AACATGAGAG GATTTTAGCC ATTGGTTTAA    2100
TTAATGAAGC CCTGGATGAA GGTGATGCCC AAAAGACTCT GCAGGCCCTA CAGATTCCTG    2160
CAGCTAAACT TGAGGGAGTC CTTGCAGAAG TGGCCCAGCA TTACCAAGAC ACGCTGATTA    2220
GAGCGAAGAG AGAGAAAGCC CAGGAAATCC AGGATGAGTC AGCTGTGTTA TGGTTGGATG    2280
AAATTCAAGG TGGAATCTGG CAGTCCAACA AAGACACCCA AGAAGCACAG AAGTTTGCCT    2340
TAGGAATCTT TGCCATTAAT GAGGCAGTAG AAAGTGGTGA TGTTGGCAAA ACACTGAGTG    2400
CCCTTCGCTC CCCTGATGTT GGCTTGTATG GAGTCATCCC TGAGTGTGGT GAAACTTACC    2460
ACAGTGATCT TGCTGAAGCC AAGAAGAAAA AACTGGCAGT AGGAGATAAT AACAGCAAGT    2520
GGGTGAAGCA CTGGGTAAAA GGTGGATATT ATTATTACCA CAATCTGGAG ACCCAGGAAG    2580
GAGGATGGGA TGAACCTCCA AATTTTGTGC AAAATTCTAT GCAGCTTTCT CGGGAGGAGA    2640
TCCAGAGTTC TATCTCTGGG GTGACTGCCG CATATAACCG AGAACAGCTG TGGCTGGCCA    2700
ATGAAGGCCT GATCACCAGG CTGCAGGCTC GCTGCCGTGG ATACTTAGTT CGACAGGAAT    2760
TCCGATCCAG GATGAATTTC CTGAAGAAAC AAATCCCTGC CATCACCTGC ATTCAGTCAC    2820
AGTGGAGAGG ATACAAGCAG AAGAAGGCAT ATCAAGATCG GTTAGCTTAC CTGCGCTCCC    2880
ACAAAGATGA AGTTGTAAAG ATTCAGTCCC TGGCAAGGAT GCACCAAGCT CGAAAGCGCT    2940
ATCGAGATCG CCTGCAGTAC TTCCGGGACC ATATAAATGA CATTATCAAA ATCCAGGCTT    3000
TTATTCGGGC AAACAAAGCT CGGGATGACT ACAAGACTCT CATCAATGCT GAGGATCCTC    3060
CTATGGTTGT GGTCCGAAAA TTTGTCCACC TGCTGGACCA AAGTGACCAG GATTTTCAGG    3120
AGGAGCTTGA CCTTATGAAG ATGCGGGAAG AGGTTATCAC CCTCATTCGT TCTAACCAGC    3180
AGCTGGAGAA TGACCTCAAT CTCATGGATA TCAAAATTGG ACTGCTAGTG AAAAATAAGA    3240
TTACGTTGCA GGATGTGGTT TCCCACAGTA AAAACTTAC CAAAAAAAAT AAGGAACAGT    3300
TGTCTGATAT GATGATGATA AATAAACAGA AGGGAGGTCT CAAGGCTTTG AGCAAGGAGA    3360
AGAGAGAGAA GTTGGAAGCT TACCAGCACC TGTTTTATTT ATTGCAAACC AATCCCACCT    3420
ATCTGGCCAA GCTCATTTTT CAGATGCCCC AGAACAAGTC CACCAAGTTC ATGGACTCTG    3480
```

FIG. 1B

```
TAATCTTCAC ACTCTACAAC TACGCGTCCA ACCAGCGAGA GGAGTACCTG CTCCTGCGGC    3540
TCTTTAAGAC AGCACTCCAA GAGGAAATCA AGTCGAAGGT AGATCAGATT CAAGAGATTG    3600
TGACAGGAAA TCCTACGGTT ATTAAAATGG TTGTAAGTTT CAACCGTGGT GCCCGTGGCC    3660
AGAATGCCCT GAGACAGATC TTGGCCCCAG TCGTGAAGGA AATTATGGAT GACAAATCTC    3720
TCAACATCAA AACTGACCCT GTGGATATTT ACAAATCTTG GGTTAATCAG ATGGAGTCTC    3780
AGACAGGAGA GGCAAGCAAA CTGCCCTATG ATGTGACCCC TGAGCAGGCG CTAGCTCATG    3840
AAGAAGTGAA GACACGGCTA GACAGCTCCA TCAGGAACAT GCGGGCTGTG ACAGACAAGT    3900
TTCTCTCAGC CATTGTCAGC TCTGTGGACA AAATCCCTTA TGGGATGCGC TTCATTGCCA    3960
AAGTGCTGAA GGACTCGTTG CATGAGAAGT TCCCTGATGC TGGTGAGGAT GAGCTGCTGA    4020
AGATTATTGG TAACTTGCTT TATTATCGAT ACATGAATCC AGCCATTGTT GCTCCTGATG    4080
CCTTTGACAT CATTGACCTG TCAGCAGGAG GCCAGCTTAC CACAGACCAA CGCCGAAATC    4140
TGGGCTCCAT TGCAAAAATG CTTCAGCATG CTGCTTCCAA TAAGATGTTT CTGGGAGATA    4200
ATGCCCACTT AAGCATCATT AATGAATATC TTTCCCAGTC CTACCAGAAA TTCAGACGGT    4260
TTTTCCAAAC TGCTTGTGAT GTCCCAGAGC TTCAGGATAA ATTTAATGTG GATGAGTACT    4320
CTGATTTAGT AACCCTCACC AAACCAGTAA TCTACATTTC CATTGGTGAA ATCATCAACA    4380
CCCACACTCT CCTGTTGGAT CACCAGGATG CCATTGCTCC GGAGCACAAT GATCCAATCC    4440
ACGAACTGCT GGACGACCTC GGCGAGGTGC CCACCATCGA GTCCCTGATA GGGGAAAGCT    4500
CTGGCAATTT AAATGACCCA ATAAGGAGG CACTGGCTAA GACGGAAGTG TCTCTCACCC    4560
TGACCAACAA GTTCGACGTG CCTGGAGATG AGAATGCAGA AATGGATGCT CGAACCATCT    4620
TACTGAATAC AAAACGTTTA ATTGTGGATG TCATCCGGTT CCAGCCAGGA GAGACCTTGA    4680
CTGAAATCCT AGAAACACCA GCCACCAGTG AACAGGAAGC AGAACATCAG AGAGCCATGC    4740
AGAGACGTGC TATCCGTGAT GCCAAAACAC CTGACAAGAT GAAAAAGTCA AAATCTGTAA    4800
AGGAAGACAG CAACCTCACT CTTCAAGAGA AGAAAGAGAA GATCCAGACA GGTTTAAAGA    4860
AGCTAACAGA GCTTGGAACC GTGGACCCAA AGAACAAATA CCAGGAACTG ATCAACGACA    4920
TTGCCAGGGA TATTCGGAAT CAGCGGAGGT ACCGACAGAG GAGAAAGGCC GAACTAGTGA    4980
AACTGCAACA GACATACGCT GCTCTGAACT CTAAGGCCAC CTTTTATGGG GAGCAGGTGG    5040
ATTACTATAA AAGCTATATC AAAACCTGCT TGGATAACTT AGCCAGCAAG GGCAAAGTCT    5100
CCAAAAAGCC TAGGGAAATG AAAGGAAAGA AAAGCAAAAA GATTTCTCTG AAATATACAG    5160
CAGCAAGACT ACATGAAAAA GGAGTTCTTC TGGAAATTGA GGACCTGCAA GTGAATCAGT    5220
TTAAAAATGT TATATTTGAA ATCAGTCCAA CAGAAGAAGT TGGAGACTTC GAAGTGAAAG    5280
CCAAATTCAT GGGAGTTCAA ATGGAGACTT TTATGTTACA TTATCAGGAC TGCTGCAGC    5340
TACAGTATGA AGGAGTTGCA GTCATGAAAT TATTTGATAG AGCTAAAGTA AATGTCAACC    5400
```

FIG. 1C

```
TCCTGATCTT CCTTCTCAAC AAAAAGTTCT ACGGGAAGTA ATTGATCGTT TGCTGCCAGC    5460
CCAGAAGGAT GAAGGAAAGA AGCACCTCAC AGCTCCTTTC TAGGTCCTTC TTTCCTCATT    5520
GGAAGCAAAG ACCTAGCCAA CAACAGCACC TCAATCTGAT ACACTCCCGA TGCCACATTT    5580
TTAACTCCTC TCGCTCTGAT GGGACATTTG TTACCCTTTT TTCATAGTGA AATTGTGTTT    5640
CAGGCTTAGT CTGACCTTTC TGGTTTCTTC ATTTTCTTCC ATTACTTAGG AAAGAGTGGA    5700
AACTCCACTA AAATTTCTCT GTGTTGTTAC AGTCTTAGAG GTTGCAGTAC TATATTGTAA    5760
GCTTTGGTGT TTGTTTAATT AGCAATAGGG ATGGTAGGAT TCAAATGTGT GTCATTTAGA    5820
AGTGGAAGCT ATTAGCACCA ATGACATAAA TACATACAAG ACACAGAACT AAAATGTCAT    5880
GTTATTAACA GTTATTAGGT TGTCATTTAA AAATAAAGTT CCTTTATATT TCTGTCCCAT    5940
CAGGAAAACT GAAGGATATG GGAATCATT GGTTATCTTC CATTGTGTTT TTCTTTATGG     6000
ACAGGAGCTA ATGAAGTGA CAGTCATGTT CAAAGGAAGC ATTTCTAGAA AAAGGAGAT      6060
AATGTTTTTA AATTTCATTA TCAAACTTGG GCAATTCTGT TTGTGTAACT CCCCGACTAG    6120
TGGATGGGAG AGTCCCATTG CTAAAATTCA GCTACTCAGA TAAATTCAGA ATGGGTCAAG    6180
GCACCTGCCT GTTTTGTTG GTGCACAGAG ATTGACTTGA TTCAGAGAGA CAATTCACTC     6240
CATCCCTATG GCAGAGGAAT GGGTTAGCCC TAATGTAGAA TGTCATTGTT TTTAAAACTG    6300
TTTTATATCT TAAGAGTGCC TTATTAAAGT ATAGATGTAT GTCTTAAAAT GTGGGTGATA    6360
GGAATTTTAA AGATTTATAT AATGCATCAA AAGCCTTAGA ATAAGAAAAG CTTTTTTTAA    6420
ATTGCTTTAT CTGTATATCT GAACTCTTGA AACTTATAGC TAAAACACTA GGATTTATCT    6480
GCAGTGTTGC AGGGAGATAA TTCTGCCTTA AATTGTCTAA AACAAAAACA AAACCAGCCA    6540
ACCTATGTTA CACGTGAGAT TAAAACCAAT TTTTTCCCCA TTTTTTCTCC TTTTTTCTCT    6600
TGCTGCCCAC ATTGTGCCTT TATTTTATGA GCCCCAGTTT TCTGGGCTTA GTTTAAAAAA    6660
AAAATCAAGT CTAAACATTG CATTTAGAAA GCTTTTGTTC TTGGATAAAA AGTCATACAC    6720
TTTAAAAAAA AAAAAAAAAC TTTTTCCAGG AAAATATATT GAAATCATGC TGCTGAGCCT    6780
CTATTTTCTT TCTTTGATGT TTTGATTCAG TATTCTTTTA TCATAAATTT TTAGCATTTA    6840
AAAATTCACT GATGTACATT AAGCCAATAA ACTGCTTTAA TGAATAACAA ACTATGTAGT    6900
GTGTCCCTAT TATAAATGCA TTGGAGAAGT ATTTTTATGA GACTCTTTAC TCAGGTGCAT    6960
GGTTACAGCC ACAGGGAGGC ATGGAGTGCC ATGGAAGGAT TCGCCACTAC CCAGACCTTG    7020
TTTTTTGTTG TATTTTGGAA GACAGGTTTT TTAAAGAAAC ATTTTCCTCA GATTAAAAGA    7080
TGATGCTATT ACAACTAGCA TTGCCTCAAA AACTGGGACC AACCAAAGTG TGTCAACCCT    7140
GTTTCCTTAA AAGAGGCTAT GAATCCCAAA GGCCACATCC AAGACAGGCA ATAATGAGCA    7200
GAGTTTACAG CTCCTTTAAT AAAATGTGTC AGTAATTTTA AGGTTTATAG TTCCCTCAAC    7260
ACAATTGCTA ATGCAGAATA GTGTAAAATG CGCTTCAAGA ATGTTGATGA TGATGATATA    7320
GAATTGTGGC TTTAGTAGCA CAGAGGATGC CCCAACAAAC TCATGGCGTT GAAACCACAC    7380
AGTTCTCATT ACTGTTATTT ATTAGCTGTA GCATTCTCTG TCTCCTCTCT CTCCTCCTTT    7440
GACCTTCTCC TCGACCAGCC ATCATGACAT TTACCATGAA TTTACTTCCT CCCAAGAGTT    7500
TGGACTGCCC GTCAGATTGT TTCTGCACAT AGTTGCCTTT GTATCTCTGT ATGAAATAAA    7560
AGGTCATTTG TTC  (SEQ ID NO: 2)                                      7573
```

FIG. 1D

MSAADEVDGLGVARPHYGSVLDNERLTAEEMDERRQNVA YEYLCHLEEAKRWMEACLGEDLPPTTELEEGLRNGVYLAK 80

LGNFFSPKVVSLKKIYDREQTRYKATGLHFRHTDNVIQWL NAMDEIGLPKIFYPETTDIYDRKNMPRCIYCIHALSLYLF 160

KIGLAPQIQDLYGKVDFTEEEINNMKTELEKYGIQMPAFS KIGGILANELSVDEAALHAAVIAINEAIDRRIPADTFAAL 240

KNPNAMLVNLEEPLASTYQDILYQAKQDKMTNAKNRTENS ERERDVYEELLTQAEIQGNINKVNTFSALANIDLALEQGD 320

ALALFRALQSPALGLRGLQQONSDWYLKQLLSDKQQKRQS GQTDPLQKEELQSGVDAANSAAQQYQRRLAAVALINAAIQ 400

KGVAEKTVLELMNPEAQLPQVYPFAADLYQKELATLQRQS PEHNLTHPELSVAVEMLSSVALINRALESGDVNTVWKQLS 480

SSVTGLTNIEEENCQRYLDELMKLKAQAHAENNEFITWND IQACDHVNLVVQEEHERILAIGLINEALDEGDAQKTLQA 560

LQIPAAKLEGVLAEVAQHYQDTLIRAKREKAQEIQDESAV LWLDEIQGGIWQSNKDTQEAQKFALGIFAINEAVESGDVG 640

KTLSALRSPDVGLYGVIPECGETYHSDLAEAKKKKLAVGD NNSKWVKHWVKGGYYYHNLETQEGGWDEPPNFVQNSMQL 720

SREEIQSSISGVTAAYNREQLWLANEGLITRLQARCRGYL VRQEFRSRMNFLKKQIPAITCIQSQWRGYKQKKAYQDRLA 800

YLRSHKDEVKIQSLARMHQARKRYRDRLQYFRDHINDII KIQAFIRANKARDDYKTLINAEDPPMVVVRKFVHLLDQSD 880

QDFQEELDLMKMREEVITLIRSNQQLENDINLMDIKIGLL VKNKITLQDVVSHSKKLTKKNKEQLSDMMINKQKGLKA 960

LSKEKREKLEAYQHLFYLLQTNPFTYLAKLIFQMPQNKSTK FMDSVIFTLYNYASNQREEYLLLRLFKTALQEEIKSKVDQ 1040

IQEIVTGNPTVIKMVVSFNRGARGQNALRQILAPVVKEIM DDKSLNIKTDPVDIYKSWVNQMESQTGEASKLPYDVTPEQ 1120

ALAHEEVKTRLDSSIRNMRAVTDKFLSAIVSSVDKIPYGM RFIAKVLKDSLHEKFPDAGEDELLKIIGNLLYYRYMNPAI 1200

VAPDAFPIIDLSAGGQLTTDQRRNLGSIAKMLQHAASNKM FLGDNAHLSIINEYLSQSYQKFRRFFQTACDVPELQDKFN 1280

VDEYSDLVTLTKPVIYISIGEIINTHTLLLDHQDAIAPEH NDPIHELLDDLGEVPTIESLIGESSGNLNDPNKEALAKTE 1360

VSLTLTNKEDVPGDENAEMDARTILLNTKRLIVDVIRFQP GETLTEILETPATSEQEAEHQRAMQRRAIRDAKTPDKMKK 1440

SKSVKEDSNLTLQEKKEKIQTGLKKLTELGTVDPKNKYQE LINDIARDIRNQRRYRQRRKAELVKLQQTYAALNSKATFY 1520

GEQVDYYKSYIKTCLDNLASKGKVSKKPREMKGKKSKKIS LKYTAARLHEKGVLLEIEDLQVNQFKNVIFEISPTEEVGD 1600

FEVKAKFMGVQMETFMLHYQDLLQLQYEGVAVMKLFDRAK VNVNLLIFLLNKKFYGK 1657

FIG. 2B (SEQ ID NO: 1)

GAP catalytic domains:

```
             +++                   ++ ++         +++              +           ++ + ++                        +
IQGAP1   ....PAIVAPDAFD IIDLSAGGQL TTDQRRNLGS IAKMLQHAAS NKMFLGDNAH ......LSII NEYLSQSYQK PRRFFQTACD   (SEQ ID NO: 3)
Sar1     ....PAIISPQTSM LLDSPDSM .......RKTLAT IAKIIQSVAN GT........ .......SST KTHLDVSFQP MLKEYEEKVH   (SEQ ID NO: 4)
Ira1     ....PALVSPDSEN III....VT. HAHDRKPFIT LAKVIQSLAM ..........GREN IFKKDILVSK EEFLKTCSDK IFNFLSELCK   (SEQ ID NO: 5)
Ira2     ....PALVSPDSEN IID....IS. HLSEKRTFIS LAKVIQNIAN ..........GSEN FSRWPALCSQ KDFLKECSDR IFRFLAELCR   (SEQ ID NO: 6)
NF1      ....PAIVSPYEAG ILD....KKP PPIERGLKL MSKILQSIAN HVLFTKEEH. ......MRPF NDFVKSNFDA ARRFFLDIAS   (SEQ ID NO: 7)
Gap1     ....PAILGPKLFD LTT....ERL DAQTSRTLTL ISKTIQSLGN LVSSRSSQQT CKEEFTVELY KKFCTEQHVD AVKHFLEVIS   (SEQ ID NO: 8)
p120GAP  ....PAILNPRMFN IIS....DSP SPIAARTLIL VAKSVQNIAN LVEFG..... AKEPY.MEGV NPFIKSNKHR MIMFLDELGN   (SEQ ID NO: 9)
Bud2     ....PVILNPKLFK YVS....QNL NETARRNLTL ISKVLLNLST LTQFANKEP. ..........WLMKM NNFIDKRHND LLDYIDKMTQ   (SEQ ID NO:10)
```

FIG. 3B

IQ motifs:

```
              +    +    +     +  III I    I
Ch.M      LAQLITRTQARCRGFLMRVEFKKMMERREC    (SEQ ID NO:11)
          IIII IIIIII:I:I II:   I:    :
745       NEGLITRLQARCRGYLVRQEFRSRMNFLKK    (SEQ ID NO:12)
775       QIPAITCIQSQWRGYKQKKAYQDRLAYLRS    (SEQ ID NO:13)
805       HKDEVVKIQSLARMHQARKRYRDRLQYFRD    (SEQ ID NO:14)
835       HINDIIKIQAFIRANKARDDYKTLINAEDP    (SEQ ID NO:15)
CONS      IXXIQXXXRXXXXRXXYXXR              (SEQ ID NO:16)
```

FIG. 3C

N-terminal repeats:

```
        I  ++ ++II+              +   +    + I      I + I +II + +
216   ALHAAVIAINEAIDRRIPADTFAALKNPNAMLVNLEEPLASTYQDILYQAKQDKMTNAK   (SEQ ID NO:17)
304   NTFSALANIDLALEQGDALALFRAIQSPALGLRGLQQQNSDWYLKQLLSDKQQKRQSGQ   (SEQ ID NO:18)
387   RRLAAVALINAAIQKGVAEKTVLELMNPEAQLPQVYPFAADLYQKELATLQRQSPEHNL   (SEQ ID NO:19)
455   EMLSSVALINRALESGDVNTVWKQLSSSVTGLTNIEEENCQRYLDELMKLKAQAHAENN   (SEQ ID NO:20)
537   ERILAIGLINEALDEGDAQKTLQALQIPAAKLEGVLAEVAQHYQDTLIRAKREKAQEIQ   (SEQ ID NO:21)
622   KFALGIFAINEAVESGDVGKTLSALRSPDVGLYGVIPECGETYHSDLAEAKKKKLAVGD   (SEQ ID NO:22)
CONS  AXXXINXAXXXGDXXXXXXXXLXXPXXXLXXXXXXXXXXYXXXLXXXK             (SEQ ID NO:23)
```

FIG. 3D

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 1657 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met Ser Ala Ala Asp Glu Val Asp Gly Leu Gly Val Ala Arg Pro His
  1               5                  10                  15

Tyr Gly Ser Val Leu Asp Asn Glu Arg Leu Thr Ala Glu Met Asp
              20                  25                  30

Glu Arg Arg Arg Gln Asn Val Ala Tyr Glu Tyr Leu Cys His Leu Glu
          35                  40                  45

Glu Ala Lys Arg Trp Met Glu Ala Cys Leu Gly Glu Asp Leu Pro Pro
 50                  55                  60

Thr Thr Glu Leu Glu Glu Gly Leu Arg Asn Gly Val Tyr Leu Ala Lys
 65                  70                  75                  80

Leu Gly Asn Phe Phe Ser Pro Lys Val Val Ser Leu Lys Lys Ile Tyr
              85                  90                  95

Asp Arg Glu Gln Thr Arg Tyr Lys Ala Thr Gly Leu His Phe Arg His
            100                 105                 110

Thr Asp Asn Val Ile Gln Trp Leu Asn Ala Met Asp Glu Ile Gly Leu
        115                 120                 125

Pro Lys Ile Phe Tyr Pro Glu Thr Thr Asp Ile Tyr Asp Arg Lys Asn
    130                 135                 140

Met Pro Arg Cys Ile Tyr Cys Ile His Ala Leu Ser Leu Tyr Leu Phe
145                 150                 155                 160

Lys Leu Gly Leu Ala Pro Gln Ile Gln Asp Leu Tyr Gly Lys Val Asp
              165                 170                 175

Phe Thr Glu Glu Glu Ile Asn Asn Met Lys Thr Glu Leu Glu Lys Tyr
            180                 185                 190

Gly Ile Gln Met Pro Ala Phe Ser Lys Ile Gly Gly Ile Leu Ala Asn
        195                 200                 205

Glu Leu Ser Val Asp Glu Ala Ala Leu His Ala Ala Val Ile Ala Ile
    210                 215                 220

Asn Glu Ala Ile Asp Arg Arg Ile Pro Ala Asp Thr Phe Ala Ala Leu
225                 230                 235                 240

Lys Asn Pro Asn Ala Met Leu Val Asn Leu Glu Glu Pro Leu Ala Ser
              245                 250                 255

Thr Tyr Gln Asp Ile Leu Tyr Gln Ala Lys Gln Asp Lys Met Thr Asn
            260                 265                 270

Ala Lys Asn Arg Thr Glu Asn Ser Glu Arg Glu Arg Asp Val Tyr Glu
        275                 280                 285

Glu Leu Leu Thr Gln Ala Glu Ile Gln Gly Asn Ile Asn Lys Val Asn
    290                 295                 300

Thr Phe Ser Ala Leu Ala Asn Ile Asp Leu Ala Leu Glu Gln Gly Asp
305                 310                 315                 320

Ala Leu Ala Leu Phe Arg Ala Leu Gln Ser Pro Ala Leu Gly Leu Arg
```

|     |     |     |     |     |     |     | 325 |     |     |     |     | 330 |     |     |     |     | 335 |     |     |
|-----|-----|-----|-----|-----|-----|-----|-----|-----|-----|-----|-----|-----|-----|-----|-----|-----|-----|-----|-----|

Gly Leu Gln Gln Gln Asn Ser Asp Trp Tyr Leu Lys Gln Leu Leu Ser
                340                 345                 350

Asp Lys Gln Gln Lys Arg Gln Ser Gly Gln Thr Asp Pro Leu Gln Lys
                355                 360                 365

Glu Glu Leu Gln Ser Gly Val Asp Ala Ala Asn Ser Ala Ala Gln Gln
        370                 375                 380

Tyr Gln Arg Arg Leu Ala Ala Val Ala Leu Ile Asn Ala Ala Ile Gln
385                 390                 395                 400

Lys Gly Val Ala Glu Lys Thr Val Leu Glu Leu Met Asn Pro Glu Ala
                405                 410                 415

Gln Leu Pro Gln Val Tyr Pro Phe Ala Ala Asp Leu Tyr Gln Lys Glu
                420                 425                 430

Leu Ala Thr Leu Gln Arg Gln Ser Pro Glu His Asn Leu Thr His Pro
                435                 440                 445

Glu Leu Ser Val Ala Val Glu Met Leu Ser Ser Val Ala Leu Ile Asn
        450                 455                 460

Arg Ala Leu Glu Ser Gly Asp Val Asn Thr Val Trp Lys Gln Leu Ser
465                 470                 475                 480

Ser Ser Val Thr Gly Leu Thr Asn Ile Glu Glu Asn Cys Gln Arg
                485                 490                 495

Tyr Leu Asp Glu Leu Met Lys Leu Lys Ala Gln Ala His Ala Glu Asn
                500                 505                 510

Asn Glu Phe Ile Thr Trp Asn Asp Ile Gln Ala Cys Val Asp His Val
        515                 520                 525

Asn Leu Val Val Gln Glu His Glu Arg Ile Leu Ala Ile Gly Leu
        530                 535                 540

Ile Asn Glu Ala Leu Asp Glu Gly Asp Ala Gln Lys Thr Leu Gln Ala
545                 550                 555                 560

Leu Gln Ile Pro Ala Ala Lys Leu Glu Gly Val Leu Ala Glu Val Ala
                565                 570                 575

Gln His Tyr Gln Asp Thr Leu Ile Arg Ala Lys Arg Glu Lys Ala Gln
                580                 585                 590

Glu Ile Gln Asp Glu Ser Ala Val Leu Trp Leu Asp Glu Ile Gln Gly
        595                 600                 605

Gly Ile Trp Gln Ser Asn Lys Asp Thr Gln Glu Ala Gln Lys Phe Ala
        610                 615                 620

Leu Gly Ile Phe Ala Ile Asn Glu Ala Val Glu Ser Gly Asp Val Gly
625                 630                 635                 640

Lys Thr Leu Ser Ala Leu Arg Ser Pro Asp Val Gly Leu Tyr Gly Val
                645                 650                 655

Ile Pro Glu Cys Gly Glu Thr Tyr His Ser Asp Leu Ala Glu Ala Lys
                660                 665                 670

Lys Lys Lys Leu Ala Val Gly Asp Asn Asn Ser Lys Trp Val Lys His
                675                 680                 685

Trp Val Lys Gly Gly Tyr Tyr Tyr His Asn Leu Glu Thr Gln Glu
        690                 695                 700

Gly Gly Trp Asp Glu Pro Pro Asn Phe Val Gln Asn Ser Met Gln Leu
705                 710                 715                 720

Ser Arg Glu Glu Ile Gln Ser Ser Ile Ser Gly Val Thr Ala Ala Tyr
                725                 730                 735

Asn Arg Glu Gln Leu Trp Leu Ala Asn Glu Gly Leu Ile Thr Arg Leu
                740                 745                 750

-continued

```
Gln Ala Arg Cys Arg Gly Tyr Leu Val Arg Gln Glu Phe Arg Ser Arg
        755                 760                 765
Met Asn Phe Leu Lys Lys Gln Ile Pro Ala Ile Thr Cys Ile Gln Ser
770                 775                 780
Gln Trp Arg Gly Tyr Lys Gln Lys Ala Tyr Gln Asp Arg Leu Ala
785                 790                 795                 800
Tyr Leu Arg Ser His Lys Asp Glu Val Val Lys Ile Gln Ser Leu Ala
                805                 810                 815
Arg Met His Gln Ala Arg Lys Arg Tyr Arg Asp Arg Leu Gln Tyr Phe
            820                 825                 830
Arg Asp His Ile Asn Asp Ile Ile Lys Ile Gln Ala Phe Ile Arg Ala
            835                 840                 845
Asn Lys Ala Arg Asp Asp Tyr Lys Thr Leu Ile Asn Ala Glu Asp Pro
        850                 855                 860
Pro Met Val Val Val Arg Lys Phe Val His Leu Leu Asp Gln Ser Asp
865                 870                 875                 880
Gln Asp Phe Gln Glu Glu Leu Asp Leu Met Lys Met Arg Glu Glu Val
                885                 890                 895
Ile Thr Leu Ile Arg Ser Asn Gln Gln Leu Glu Asn Asp Leu Asn Leu
            900                 905                 910
Met Asp Ile Lys Ile Gly Leu Leu Val Lys Asn Lys Ile Thr Leu Gln
            915                 920                 925
Asp Val Val Ser His Ser Lys Lys Leu Thr Lys Lys Asn Lys Glu Gln
        930                 935                 940
Leu Ser Asp Met Met Met Ile Asn Lys Gln Lys Gly Gly Leu Lys Ala
945                 950                 955                 960
Leu Ser Lys Glu Lys Arg Glu Lys Leu Glu Ala Tyr Gln His Leu Phe
                965                 970                 975
Tyr Leu Leu Gln Thr Asn Pro Thr Tyr Leu Ala Lys Leu Ile Phe Gln
            980                 985                 990
Met Pro Gln Asn Lys Ser Thr Lys Phe Met Asp Ser Val Ile Phe Thr
            995                 1000                1005
Leu Tyr Asn Tyr Ala Ser Asn Gln Arg Glu Glu Tyr Leu Leu Leu Arg
        1010                1015                1020
Leu Phe Lys Thr Ala Leu Gln Glu Glu Ile Lys Ser Lys Val Asp Gln
1025                1030                1035                1040
Ile Gln Glu Ile Val Thr Gly Asn Pro Thr Val Ile Lys Met Val Val
                1045                1050                1055
Ser Phe Asn Arg Gly Ala Arg Gly Gln Asn Ala Leu Arg Gln Ile Leu
            1060                1065                1070
Ala Pro Val Val Lys Glu Ile Met Asp Asp Lys Ser Leu Asn Ile Lys
        1075                1080                1085
Thr Asp Pro Val Asp Ile Tyr Lys Ser Trp Val Asn Gln Met Glu Ser
        1090                1095                1100
Gln Thr Gly Glu Ala Ser Lys Leu Pro Tyr Asp Val Thr Pro Glu Gln
1105                1110                1115                1120
Ala Leu Ala His Glu Glu Val Lys Thr Arg Leu Asp Ser Ser Ile Arg
                1125                1130                1135
Asn Met Arg Ala Val Thr Asp Lys Phe Leu Ser Ala Ile Val Ser Ser
            1140                1145                1150
Val Asp Lys Ile Pro Tyr Gly Met Arg Phe Ile Ala Lys Val Leu Lys
            1155                1160                1165
Asp Ser Leu His Glu Lys Phe Pro Asp Ala Gly Glu Asp Glu Leu Leu
        1170                1175                1180
```

-continued

Lys Ile Ile Gly Asn Leu Leu Tyr Tyr Arg Tyr Met Asn Pro Ala Ile
1185                1190                1195                1200

Val Ala Pro Asp Ala Phe Asp Ile Ile Asp Leu Ser Ala Gly Gly Gln
            1205                1210                1215

Leu Thr Thr Asp Gln Arg Arg Asn Leu Gly Ser Ile Ala Lys Met Leu
            1220                1225                1230

Gln His Ala Ala Ser Asn Lys Met Phe Leu Gly Asp Asn Ala His Leu
            1235                1240                1245

Ser Ile Ile Asn Glu Tyr Leu Ser Gln Ser Tyr Gln Lys Phe Arg Arg
            1250                1255                1260

Phe Phe Gln Thr Ala Cys Asp Val Pro Glu Leu Gln Asp Lys Phe Asn
1265                1270                1275                1280

Val Asp Glu Tyr Ser Asp Leu Val Thr Leu Thr Lys Pro Val Ile Tyr
                1285                1290                1295

Ile Ser Ile Gly Glu Ile Ile Asn Thr His Thr Leu Leu Leu Asp His
            1300                1305                1310

Gln Asp Ala Ile Ala Pro Glu His Asn Asp Pro Ile His Glu Leu Leu
            1315                1320                1325

Asp Asp Leu Gly Glu Val Pro Thr Ile Glu Ser Leu Ile Gly Glu Ser
            1330                1335                1340

Ser Gly Asn Leu Asn Asp Pro Asn Lys Glu Ala Leu Ala Lys Thr Glu
1345                1350                1355                1360

Val Ser Leu Thr Leu Thr Asn Lys Phe Asp Val Pro Gly Asp Glu Asn
                1365                1370                1375

Ala Glu Met Asp Ala Arg Thr Ile Leu Leu Asn Thr Lys Arg Leu Ile
                1380                1385                1390

Val Asp Val Ile Arg Phe Gln Pro Gly Glu Thr Leu Thr Glu Ile Leu
            1395                1400                1405

Glu Thr Pro Ala Thr Ser Glu Gln Glu Ala Glu His Gln Arg Ala Met
            1410                1415                1420

Gln Arg Arg Ala Ile Arg Asp Ala Lys Thr Pro Asp Lys Met Lys Lys
1425                1430                1435                1440

Ser Lys Ser Val Lys Glu Asp Ser Asn Leu Thr Leu Gln Glu Lys Lys
                1445                1450                1455

Glu Lys Ile Gln Thr Gly Leu Lys Lys Leu Thr Glu Leu Gly Thr Val
            1460                1465                1470

Asp Pro Lys Asn Lys Tyr Gln Glu Leu Ile Asn Asp Ile Ala Arg Asp
            1475                1480                1485

Ile Arg Asn Gln Arg Arg Tyr Arg Gln Arg Arg Lys Ala Glu Leu Val
            1490                1495                1500

Lys Leu Gln Gln Thr Tyr Ala Ala Leu Asn Ser Lys Ala Thr Phe Tyr
1505                1510                1515                1520

Gly Glu Gln Val Asp Tyr Tyr Lys Ser Tyr Ile Lys Thr Cys Leu Asp
                1525                1530                1535

Asn Leu Ala Ser Lys Gly Lys Val Ser Lys Lys Pro Arg Glu Met Lys
            1540                1545                1550

Gly Lys Lys Ser Lys Lys Ile Ser Leu Lys Tyr Thr Ala Ala Arg Leu
            1555                1560                1565

His Glu Lys Gly Val Leu Leu Glu Ile Glu Asp Leu Gln Val Asn Gln
            1570                1575                1580

Phe Lys Asn Val Ile Phe Glu Ile Ser Pro Thr Glu Glu Val Gly Asp
1585                1590                1595                1600

Phe Glu Val Lys Ala Lys Phe Met Gly Val Gln Met Glu Thr Phe Met

|     |     |     |     |     |     |
| --- | --- | --- | --- | --- | --- |
|     | 1605 |     | 1610 |     | 1615 |

Leu His Tyr Gln Asp Leu Leu Gln Leu Gln Tyr Glu Gly Val Ala Val
          1620                      1625                    1630

Met Lys Leu Phe Asp Arg Ala Lys Val Asn Val Asn Leu Leu Ile Phe
          1635                      1640                    1645

Leu Leu Asn Lys Lys Phe Tyr Gly Lys
          1650                      1655

( 2 ) INFORMATION FOR SEQ ID NO:2:

( i ) SEQUENCE CHARACTERISTICS:
        ( A ) LENGTH: 7573 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| GGTATTAAAA | CTGATCTTTT | GACATTTTTG | ACAATGTTCT | TATAAATTAC | TTTCTTTTTT | 60 |
| ATCATATATG | GATGGGATGA | AGCACAGAGT | AAGATAGAGT | GCACAGCAAA | GGGGATCTGC | 120 |
| CCCTCCTATC | TGTCCAATAC | CCCACAGGTT | TTGGTGATAA | TCTTGGGCAA | TGTTCCAGTC | 180 |
| AAACCTGCCT | CCCACTTCTC | ACTAAAGTTA | GTGAACATGT | GACCCACATT | CCCCAAATAA | 240 |
| GAGCCTCTTA | TAAACTCCAT | TCTTGGCTTT | TTCATTCATA | GAGATAGCTA | TTTTATGAGA | 300 |
| CATAGATAAA | GCATTTTTTA | GTGATGTGCA | CGATGCCTTT | TTTCTTAATT | ATTAACTTCT | 360 |
| CAAAACATAA | ACACATTGGA | GGCACTTAAT | AAAGGGAGCT | GTACGTACCG | CCGTCCGCGC | 420 |
| CTCCAAGGTT | TCACGGCTTC | CTCAGCAGAG | ACTCGGGCTC | GTCCGCCATG | TCCGCCGCAG | 480 |
| ACGAGGTTGA | CGGGCTGGGC | GTGGCCCGGC | CGCACTATGG | CTCTGTCCTG | GATAATGAAA | 540 |
| GACTTACTGC | AGAGGAGATG | GATGAAAGGA | GACGTCAGAA | CGTGGCTTAT | GAGTACCTTT | 600 |
| GTCATTGGA | AGAAGCGAAG | AGGTGGATGG | AAGCATGCCT | AGGGGAAGAT | CTGCCTCCCA | 660 |
| CCACAGAACT | GGAGGAGGGG | CTTAGGAATG | GGGTCTACCT | TGCCAAACTG | GGGAACTTCT | 720 |
| TCTCTCCCAA | AGTAGTGTCC | CTGAAAAAAA | TCTATGATCG | AGAACAGACC | AGATACAAGG | 780 |
| CGACTGGCCT | CCACTTTAGA | CACACTGATA | ATGTGATTCA | GTGGTTGAAT | GCCATGGATG | 840 |
| AGATTGGATT | GCCTAAGATT | TTTTACCCAG | AAACTACAGA | TATCTATGAT | CGAAAGAACA | 900 |
| TGCCAAGATG | TATCTACTGT | ATCCATGCAC | TCAGTTTGTA | CCTGTTCAAG | CTAGGCCTGG | 960 |
| CCCCTCAGAT | TCAAGACCTA | TATGGAAAGG | TTGACTTCAC | AGAAGAAGAA | ATCAACAACA | 1020 |
| TGAAGACTGA | GTTGGAGAAG | TATGGCATCC | AGATGCCTGC | CTTTAGCAAG | ATTGGGGGCA | 1080 |
| TCTTGGCTAA | TGAACTGTCA | GTGGATGAAG | CCGCATTACA | TGCTGCTGTT | ATTGCTATTA | 1140 |
| ATGAAGCTAT | TGACCGTAGA | ATTCCAGCCG | ACACATTTGC | AGCTTTGAAA | AATCCGAATG | 1200 |
| CCATGCTTGT | AAATCTTGAA | GAGCCCTTGG | CATCCACTTA | CCAGGATATA | CTTTACCAGG | 1260 |
| CTAAGCAGGA | CAAAATGACA | AATGCTAAAA | ACAGGACAGA | AAACTCAGAG | AGAGAAAGAG | 1320 |
| ATGTTTATGA | GGAGCTGCTC | ACGCAAGCTG | AAATTCAAGG | CAATATAAAC | AAAGTCAATA | 1380 |
| CATTTCTGC | ATTAGCAAAT | ATCGACCTGG | CTTTAGAACA | AGGAGATGCA | CTGGCCTTGT | 1440 |
| TCAGGGCTCT | GCAGTCACCA | GCCCTGGGGC | TTCGAGGACT | GCAGCAACAG | AATAGCGACT | 1500 |
| GGTACTTGAA | GCAGCTCCTG | AGTGATAAAC | AGCAGAAGAG | ACAGAGTGGT | CAGACTGACC | 1560 |
| CCCTGCAGAA | GGAGGAGCTG | CAGTCTGGAG | TGGATGCTGC | AAACAGTGCT | GCCCAGCAAT | 1620 |
| ATCAGAGAAG | ATTGGCAGCA | GTAGCACTGA | TTAATGCTGC | AATCCAGAAG | GGTGTTGCTG | 1680 |

```
AGAAGACTGT TTTGGAACTG ATGAATCCCG AAGCCCAGCT GCCCCAGGTG TATCCATTTG   1740
CCGCCGATCT CTATCAGAAG GAGCTGGCTA CCCTGCAGCG ACAAAGTCCT GAACATAATC   1800
TCACCCACCC AGAGCTCTCT GTCGCAGTGG AGATGTTGTC ATCGGTGGCC CTGATCAACA   1860
GGGCATTGGA ATCAGGAGAT GTGAATACAG TGTGGAAGCA ATTGAGCAGT TCAGTTACTG   1920
GTCTTACCAA TATTGAGGAA GAAAACTGTC AGAGGTATCT CGATGAGTTG ATGAAACTGA   1980
AGGCTCAGGC ACATGCAGAG AATAATGAAT TCATTACATG GAATGATATC CAAGCTTGCG   2040
TGGACCATGT GAACCTGGTG GTGCAAGAGG AACATGAGAG GATTTTAGCC ATTGGTTTAA   2100
TTAATGAAGC CCTGGATGAA GGTGATGCCC AAAAGACTCT GCAGGCCCTA CAGATTCCTG   2160
CAGCTAAACT TGAGGGAGTC CTTGCAGAAG TGGCCCAGCA TTACCAAGAC ACGCTGATTA   2220
GAGCGAAGAG AGAGAAAGCC CAGGAAATCC AGGATGAGTC AGCTGTGTTA TGGTTGGATG   2280
AAATTCAAGG TGGAATCTGG CAGTCCAACA AAGACACCCA AGAAGCACAG AAGTTTGCCT   2340
TAGGAATCTT TGCCATTAAT GAGGCAGTAG AAAGTGGTGA TGTTGGCAAA ACACTGAGTG   2400
CCCTTCGCTC CCCTGATGTT GGCTTGTATG GAGTCATCCC TGAGTGTGGT GAAACTTACC   2460
ACAGTGATCT TGCTGAAGCC AAGAAGAAAA AACTGGCAGT AGGAGATAAT AACAGCAAGT   2520
GGGTGAAGCA CTGGGTAAAA GGTGGATATT ATTATTACCA CAATCTGGAG ACCCAGGAAG   2580
GAGGATGGGA TGAACCTCCA AATTTTGTGC AAAATTCTAT GCAGCTTTCT CGGGAGGAGA   2640
TCCAGAGTTC TATCTCTGGG GTGACTGCCG CATATAACCG AGAACAGCTG TGGCTGGCCA   2700
ATGAAGGCCT GATCACCAGG CTGCAGGCTC GCTGCCGTGG ATACTTAGTT CGACAGGAAT   2760
TCCGATCCAG GATGAATTTC CTGAAGAAAC AAATCCCTGC CATCACCTGC ATTCAGTCAC   2820
AGTGGAGAGG ATACAAGCAG AAGAAGGCAT ATCAAGATCG GTTAGCTTAC CTGCGCTCCC   2880
ACAAAGATGA AGTTGTAAAG ATTCAGTCCC TGGCAAGGAT GCACCAAGCT CGAAAGCGCT   2940
ATCGAGATCG CCTGCAGTAC TTCCGGGACC ATATAAATGA CATTATCAAA ATCCAGGCTT   3000
TTATTCGGGC AAACAAAGCT CGGGATGACT ACAAGACTCT CATCAATGCT GAGGATCCTC   3060
CTATGGTTGT GGTCCGAAAA TTTGTCCACC TGCTGGACCA AAGTGACCAG GATTTTCAGG   3120
AGGAGCTTGA CCTTATGAAG ATGCGGGAAG AGGTTATCAC CCTCATTCGT TCTAACCAGC   3180
AGCTGGAGAA TGACCTCAAT CTCATGGATA TCAAAATTGG ACTGCTAGTG AAAAATAAGA   3240
TTACGTTGCA GGATGTGGTT TCCCACAGTA AAAACTTAC CAAAAAAAAT AAGGAACAGT   3300
TGTCTGATAT GATGATGATA AATAAACAGA AGGGAGGTCT CAAGGCTTTG AGCAAGGAGA   3360
AGAGAGAGAA GTTGGAAGCT TACCAGCACC TGTTTTATTT ATTGCAAACC AATCCCACCT   3420
ATCTGGCCAA GCTCATTTTT CAGATGCCCC AGAACAAGTC CACCAAGTTC ATGGACTCTG   3480
TAATCTTCAC ACTCTACAAC TACGCGTCCA ACCAGCGAGA GGAGTACCTG CTCCTGCGGC   3540
TCTTTAAGAC AGCACTCCAA GAGGAAATCA AGTCGAAGGT AGATCAGATT CAAGAGATTG   3600
TGACAGGAAA TCCTACGGTT ATTAAATGG TTGTAAGTTT CAACCGTGGT GCCCGTGGCC   3660
AGAATGCCCT GAGACAGATC TTGGCCCCAG TCGTGAAGGA AATTATGGAT GACAAATCTC   3720
TCAACATCAA AACTGACCCT GTGGATATTT ACAAATCTTG GGTTAATCAG ATGGAGTCTC   3780
AGACAGGAGA GGCAAGCAAA CTGCCCTATG ATGTGACCCC TGAGCAGGCG CTAGCTCATG   3840
AAGAAGTGAA GACACGGCTA GACAGCTCCA TCAGGAACAT GCGGGCTGTG ACAGACAAGT   3900
TTCTCTCAGC CATTGTCAGC TCTGTGGACA AAATCCCTTA TGGGATGCGC TTCATTGCCA   3960
AAGTGCTGAA GGACTCGTTG CATGAGAAGT TCCCTGATGC TGGTGAGGAT GAGCTGCTGA   4020
AGATTATTGG TAACTTGCTT TATTATCGAT ACATGAATCC AGCCATTGTT GCTCCTGATG   4080
```

```
CCTTTGACAT CATTGACCTG TCAGCAGGAG GCCAGCTTAC CACAGACCAA CGCCGAAATC      4140
TGGGCTCCAT TGCAAAAATG CTTCAGCATG CTGCTTCCAA TAAGATGTTT CTGGGAGATA      4200
ATGCCCACTT AAGCATCATT AATGAATATC TTTCCCAGTC CTACCAGAAA TTCAGACGGT      4260
TTTTCCAAAC TGCTTGTGAT GTCCCAGAGC TTCAGGATAA ATTTAATGTG GATGAGTACT      4320
CTGATTTAGT AACCCTCACC AAACCAGTAA TCTACATTTC CATTGGTGAA ATCATCAACA      4380
CCCACACTCT CCTGTTGGAT CACCAGGATG CCATTGCTCC GGAGCACAAT GATCCAATCC      4440
ACGAACTGCT GGACGACCTC GGCGAGGTGC CCACCATCGA GTCCCTGATA GGGGAAAGCT      4500
CTGGCAATTT AAATGACCCA ATAAGGAGG CACTGGCTAA GACGGAAGTG TCTCTCACCC        4560
TGACCAACAA GTTCGACGTG CCTGGAGATG AGAATGCAGA AATGGATGCT CGAACCATCT      4620
TACTGAATAC AAAACGTTTA ATTGTGGATG TCATCCGGTT CCAGCCAGGA GAGACCTTGA      4680
CTGAAATCCT AGAAACACCA GCCACCAGTG AACAGGAAGC AGAACATCAG AGAGCCATGC      4740
AGAGACGTGC TATCCGTGAT GCCAAAACAC CTGACAAGAT GAAAAGTCA AAATCTGTAA        4800
AGGAAGACAG CAACCTCACT CTTCAAGAGA AGAAAGAGAA GATCCAGACA GGTTTAAAGA      4860
AGCTAACAGA GCTTGGAACC GTGGACCCAA AGAACAAATA CCAGGAACTG ATCAACGACA      4920
TTGCCAGGGA TATTCGGAAT CAGCGGAGGT ACCGACAGAG GAGAAAGGCC GAACTAGTGA      4980
AACTGCAACA GACATACGCT GCTCTGAACT CTAAGGCCAC CTTTTATGGG GAGCAGGTGG      5040
ATTACTATAA AAGCTATATC AAAACCTGCT TGGATAACTT AGCCAGCAAG GGCAAAGTCT      5100
CCAAAAAGCC TAGGGAAATG AAAGGAAAGA AAGCAAAAA GATTTCTCTG AAATATACAG        5160
CAGCAAGACT ACATGAAAAA GGAGTTCTTC TGGAAATTGA GGACCTGCAA GTGAATCAGT      5220
TTAAAAATGT TATATTTGAA ATCAGTCCAA CAGAAGAAGT TGGAGACTTC GAAGTGAAAG      5280
CCAAATTCAT GGGAGTTCAA ATGGAGACTT TTATGTTACA TTATCAGGAC CTGCTGCAGC      5340
TACAGTATGA AGGAGTTGCA GTCATGAAAT TATTTGATAG AGCTAAAGTA AATGTCAACC      5400
TCCTGATCTT CCTTCTCAAC AAAAAGTTCT ACGGGAAGTA ATTGATCGTT TGCTGCCAGC      5460
CCAGAAGGAT GAAGGAAAGA AGCACCTCAC AGCTCCTTTC TAGGTCCTTC TTTCCTCATT      5520
GGAAGCAAAG ACCTAGCCAA CAACAGCACC TCAATCTGAT ACACTCCCGA TGCCACATTT      5580
TTAACTCCTC TCGCTCTGAT GGGACATTTG TTACCCTTTT TTCATAGTGA AATTGTGTTT      5640
CAGGCTTAGT CTGACCTTTC TGGTTTCTTC ATTTTCTTCC ATTACTTAGG AAAGAGTGGA      5700
AACTCCACTA AAATTTCTCT GTGTTGTTAC AGTCTTAGAG GTTGCAGTAC TATATTGTAA      5760
GCTTTGGTGT TTGTTTAATT AGCAATAGGG ATGGTAGGAT TCAAATGTGT GTCATTTAGA      5820
AGTGGAAGCT ATTAGCACCA ATGACATAAA TACATACAAG ACACAGAACT AAAATGTCAT      5880
GTTATTAACA GTTATTAGGT TGTCATTTAA AAATAAAGTT CCTTTATATT TCTGTCCCAT      5940
CAGGAAAACT GAAGGATATG GGAATCATT GGTTATCTTC CATTGTGTTT TTCTTTATGG        6000
ACAGGAGCTA ATGGAAGTGA CAGTCATGTT CAAAGGAAGC ATTTCTAGAA AAAGGAGAT        6060
AATGTTTTTA AATTTCATTA TCAAACTTGG GCAATTCTGT TTGTGTAACT CCCCGACTAG      6120
TGGATGGGAG AGTCCCATTG CTAAAATTCA GCTACTCAGA TAAATTCAGA ATGGGTCAAG      6180
GCACCTGCCT GTTTTGTTG GTGCACAGAG ATTGACTTGA TTCAGAGAGA CAATTCACTC        6240
CATCCCTATG GCAGAGGAAT GGGTTAGCCC TAATGTAGAA TGTCATTGTT TTTAAAACTG      6300
TTTTATATCT TAAGAGTGCC TTATTAAAGT ATAGATGTAT GTCTTAAAAT GTGGGTGATA      6360
GGAATTTTAA AGATTTATAT AATGCATCAA AAGCCTTAGA ATAAGAAAAG CTTTTTTTAA      6420
ATTGCTTTAT CTGTATATCT GAACTCTTGA AACTTATAGC TAAAACACTA GGATTTATCT      6480
```

| | | | | | |
|---|---|---|---|---|---|
| GCAGTGTTGC | AGGGAGATAA | TTCTGCCTTA | AATTGTCTAA | AACAAAAACA | AAACCAGCCA | 6540 |
| ACCTATGTTA | CACGTGAGAT | TAAAACCAAT | TTTTTCCCCA | TTTTTTCTCC | TTTTTTCTCT | 6600 |
| TGCTGCCCAC | ATTGTGCCTT | TATTTTATGA | GCCCCAGTTT | TCTGGGCTTA | GTTTAAAAAA | 6660 |
| AAAATCAAGT | CTAAACATTG | CATTTAGAAA | GCTTTGTTC | TTGGATAAAA | AGTCATACAC | 6720 |
| TTTAAAAAAA | AAAAAAAAAC | TTTTCCAGG | AAAATATATT | GAAATCATGC | TGCTGAGCCT | 6780 |
| CTATTTTCTT | TCTTTGATGT | TTTGATTCAG | TATTCTTTTA | TCATAAATTT | TTAGCATTTA | 6840 |
| AAAATTCACT | GATGTACATT | AAGCCAATAA | ACTGCTTTAA | TGAATAACAA | ACTATGTAGT | 6900 |
| GTGTCCCTAT | TATAAATGCA | TTGGAGAAGT | ATTTTATGA | GACTCTTTAC | TCAGGTGCAT | 6960 |
| GGTTACAGCC | ACAGGGAGGC | ATGGAGTGCC | ATGGAAGGAT | TCGCCACTAC | CCAGACCTTG | 7020 |
| TTTTTTGTTG | TATTTTGGAA | GACAGGTTTT | TTAAAGAAAC | ATTTTCCTCA | GATTAAAAGA | 7080 |
| TGATGCTATT | ACAACTAGCA | TTGCCTCAAA | AACTGGGACC | AACCAAAGTG | TGTCAACCCT | 7140 |
| GTTTCCTTAA | AAGAGGCTAT | GAATCCCAAA | GGCCACATCC | AAGACAGGCA | ATAATGAGCA | 7200 |
| GAGTTTACAG | CTCCTTTAAT | AAAATGTGTC | AGTAATTTTA | AGGTTTATAG | TTCCCTCAAC | 7260 |
| ACAATTGCTA | ATGCAGAATA | GTGTAAAATG | CGCTTCAAGA | ATGTTGATGA | TGATGATATA | 7320 |
| GAATTGTGGC | TTTAGTAGCA | CAGAGGATGC | CCCAACAAAC | TCATGGCGTT | GAAACCACAC | 7380 |
| AGTTCTCATT | ACTGTTATTT | ATTAGCTGTA | GCATTCTCTG | TCTCCTCTCT | CTCCTCCTTT | 7440 |
| GACCTTCTCC | TCGACCAGCC | ATCATGACAT | TTACCATGAA | TTTACTTCCT | CCCAAGAGTT | 7500 |
| TGGACTGCCC | GTCAGATTGT | TTCTGCACAT | AGTTGCCTTT | GTATCTCTGT | ATGAAATAAA | 7560 |
| AGGTCATTTG | TTC | | | | | 7573 |

( 2 ) INFORMATION FOR SEQ ID NO:3:

( i ) SEQUENCE CHARACTERISTICS:
( A ) LENGTH: 274 amino acids
( B ) TYPE: amino acid
( D ) TOPOLOGY: linear ( i i ) MOLECULE TYPE: peptide ( x i ) SEQUENCE DESCRIPTION: SEQ ID NO:3:

```
Ser Thr Lys Phe Met Asp Ser Val Ile Phe Thr Leu Tyr Asn Tyr Ala
  1               5                  10                  15

Ser Asn Gln Arg Glu Glu Tyr Leu Leu Arg Leu Phe Lys Thr Ala
                 20                  25                  30

Leu Gln Glu Glu Ile Lys Ser Lys Val Asp Gln Ile Gln Glu Ile Val
                 35                  40                  45

Thr Gly Met Pro Thr Val Ile Lys Met Val Val Ser Phe Asn Arg Gly
 50                      55                      60

Ala Arg Gln Gln Asn Ala Leu Arg Gln Ile Leu Ala Pro Val Val Lys
 65                  70                      75                  80

Glu Ile Met Asp Asp Lys Ser Leu Asn Ile Lys Thr Asp Pro Val Asp
                         85                  90                  95

Ile Tyr Lys Ser Trp Val Asn Gln Met Glu Ser Gln Thr Gly Glu Ala
                    100                 105                 110

Ser Lys Leu Pro Tyr Asp Val Thr Pro Glu Gln Ala Leu Ala His Glu
                115                 120                 125

Glu Val Lys Thr Arg Leu Asp Ser Ser Ile Arg Asn Met Arg Ala Val
            130                 135                 140

Thr Asp Lys Phe Leu Ser Ala Ile Val Ser Ser Val Asp Lys Ile Pro
145                 150                 155                 160
```

| | | | | | | | | | | | | | | |
|---|---|---|---|---|---|---|---|---|---|---|---|---|---|---|
| Tyr | Gly | Met | Arg | Phe 165 | Ile | Ala | Lys | Val | Leu 170 | Lys | Asp | Ser | Leu | His 175 | Glu |
| Lys | Phe | Pro | Asp 180 | Ala | Gly | Glu | Asp | Glu 185 | Leu | Leu | Lys | Ile | Ile 190 | Gly | Asn |
| Leu | Leu | Tyr 195 | Tyr | Arg | Tyr | Met | Asn 200 | Pro | Ala | Ile | Val | Ala 205 | Pro | Asp | Ala |
| Phe | Asp 210 | Ile | Ile | Asp | Leu | Ser 215 | Ala | Gly | Gly | Gln | Leu 220 | Thr | Thr | Asp | Gln |
| Arg 225 | Arg | Asn | Leu | Gly | Ser 230 | Ile | Ala | Lys | Met | Leu 235 | Gln | His | Ala | Ala | Ser 240 |
| Asn | Lys | Met | Phe | Leu 245 | Gly | Asp | Asn | Ala | His 250 | Leu | Ser | Ile | Ile | Asn 255 | Glu |
| Tyr | Leu | Ser | Gln 260 | Ser | Tyr | Gln | Lys | Phe 265 | Arg | Arg | Phe | Phe | Gln 270 | Thr | Ala |
| Cys | Asp | | | | | | | | | | | | | | |

( 2 ) INFORMATION FOR SEQ ID NO:4:

( i ) SEQUENCE CHARACTERISTICS:
        ( A ) LENGTH: 257 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

| | | | | | | | | | | | | | | |
|---|---|---|---|---|---|---|---|---|---|---|---|---|---|---|
| Met 1 | Asp | Ala | Leu | Leu 5 | Gln | Ile | Val | Met | Phe 10 | Asn | Ile | Tyr | Gly | Asn 15 | Gln |
| Tyr | Glu | Ser | Arg 20 | Glu | Glu | His | Leu | Leu 25 | Ser | Leu | Phe | Gln | Met 30 | Val |
| Leu | Thr | Thr 35 | Lys | Phe | Glu | Ala | Thr 40 | Ser | Asp | Val | Leu | Ser 45 | Leu | Leu | Arg |
| Ala | Met 50 | Thr | Pro | Val | Ser | Arg 55 | Met | Leu | Thr | Thr | Tyr 60 | Thr | Arg | Arg | Gly |
| Pro 65 | Gln | Gln | Ala | Tyr | Leu 70 | Arg | Ser | Ile | Leu | Tyr 75 | Gln | Cys | Ile | Asn | Asp 80 |
| Val | Ala | Ile | His | Pro 85 | Asp | Leu | Gln | Leu | Asp 90 | Ile | His | Pro | Leu | Ser 95 | Val |
| Tyr | Arg | Tyr | Leu 100 | Val | Asn | Thr | Gly | Gln 105 | Leu | Ser | Pro | Ser | Glu 110 | Asp | Asp |
| Asn | Leu | Leu 115 | Thr | Asn | Glu | Glu | Val 120 | Ser | Glu | Phe | Pro | Ala 125 | Val | Lys | Asn |
| Ala | Ile 130 | Gln | Glu | Arg | Ser | Ala 135 | Gln | Leu | Leu | Leu | Leu 140 | Thr | Lys | Arg | Phe |
| Leu 145 | Asp | Ala | Val | Leu | Asn 150 | Ser | Ile | Asp | Glu | Ile 155 | Pro | Tyr | Gly | Ile | Arg 160 |
| Trp | Val | Cys | Lys | Leu 165 | Ile | Arg | Asn | Leu | Thr 170 | Asn | Arg | Leu | Phe | Pro 175 | Ser |
| Ile | Ser | Asp | Ser 180 | Thr | Ile | Cys | Ser | Leu 185 | Ile | Gly | Gly | Phe | Phe 190 | Leu |
| Arg | Phe | Val 195 | Asn | Pro | Ala | Ile | Ile 200 | Ser | Pro | Gln | Thr | Ser 205 | Met | Leu | Leu |
| Asp | Ser 210 | Cys | Pro | Ser | Asp | Asn 215 | Val | Arg | Lys | Thr | Leu 220 | Ala | Thr | Ile | Ala |
| Lys 225 | Ile | Ile | Gln | Ser | Val 230 | Ala | Asn | Gly | Thr | Ser 235 | Ser | Thr | Lys | Thr | His 240 |

```
Leu Asp Val Ser Phe Gln Pro Asn Leu Lys Glu Tyr Glu Glu Lys Val
                245                 250                 255

His ( 2 ) INFORMATION FOR SEQ ID NO:5:

( i ) SEQUENCE CHARACTERISTICS:
        ( A ) LENGTH: 224 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Asp Val Asp Leu Tyr Ala Gly Gly Phe Leu Asn Ala Phe Asp Thr Arg
1               5                   10                  15

Asn Ala Ser His Ile Leu Val Thr Glu Leu Leu Lys Gln Glu Ile Lys
                20                  25                  30

Arg Ala Ala Arg Ser Asp Asp Ile Leu Arg Arg Asn Ser Cys Ala Thr
                35                  40                  45

Arg Ala Leu Ser Leu Tyr Thr Arg Ser Arg Gly Asn Lys Tyr Leu Ile
        50                  55                  60

Lys Thr Leu Arg Pro Val Leu Gln Gly Ile Val Asp Asn Lys Glu Ser
65                  70                  75                  80

Phe Glu Ile Asp Lys Met Lys Pro Gly Ser Glu Asn Ser Glu Lys Met
                85                  90                  95

Leu Asp Leu Phe Glu Lys Tyr Met Thr Arg Leu Ile Asp Ala Ile Thr
                100                 105                 110

Ser Ser Ile Asp Asp Phe Pro Ile Glu Leu Val Asp Ile Cys Lys Thr
            115                 120                 125

Ile Tyr Asn Ala Ala Ser Val Asn Phe Pro Glu Tyr Ala Tyr Ile Ala
    130                 135                 140

Val Gly Ser Phe Val Phe Leu Arg Phe Ile Gly Pro Ala Leu Val Ser
145                 150                 155                 160

Pro Asp Ser Glu Asn Ile Ile Ile Val Thr His Ala His Asp Arg Lys
                165                 170                 175

Pro Phe Ile Thr Leu Ala Lys Val Ile Gln Ser Leu Ala Asn Gly Arg
            180                 185                 190

Glu Asn Ile Phe Lys Lys Asp Ile Leu Val Ser Lys Glu Glu Phe Leu
        195                 200                 205

Lys Thr Cys Ser Asp Lys Ile Phe Asn Phe Leu Ser Glu Leu Cys Lys
    210                 215                 220

( 2 ) INFORMATION FOR SEQ ID NO:6:

( i ) SEQUENCE CHARACTERISTICS:
        ( A ) LENGTH: 224 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Asp Ile Asp Ala Tyr Ala Ala Gly Leu Ile Asn Ala Phe Glu Thr Arg
1               5                   10                  15

Asn Ala Thr His Ile Val Val Ala Gln Leu Ile Lys Asn Glu Ile Glu
                20                  25                  30

Lys Ser Ser Arg Pro Thr Asp Ile Leu Arg Arg Met Ser Cys Ala Thr
            35                  40                  45
```

```
Arg  Ser  Leu  Ser  Met  Leu  Ala  Arg  Ser  Lys  Gln  Asn  Glu  Tyr  Leu  Ile
     50                      55                      60

Arg  Thr  Leu  Gln  Pro  Leu  Leu  Lys  Lys  Ile  Ile  Gln  Asn  Arg  Asp  Phe
65                            70                      75                      80

Phe  Lys  Ile  Glu  Lys  Leu  Lys  Pro  Glu  Asp  Ser  Asp  Ala  Glu  Arg  Gln
                    85                      90                           95

Ile  Glu  Leu  Phe  Val  Lys  Tyr  Met  Asn  Glu  Leu  Leu  Glu  Ser  Ile  Ser
               100                      105                     110

Asn  Ser  Val  Ser  Tyr  Phe  Pro  Pro  Leu  Phe  Tyr  Ile  Cys  Gln  Asn
          115                      120                     125

Ile  Tyr  Lys  Val  Ala  Cys  Glu  Lys  Phe  Pro  Asp  His  Ala  Ile  Ile  Ala
     130                      135                          140

Ala  Gly  Ser  Phe  Val  Phe  Leu  Arg  Phe  Phe  Cys  Pro  Ala  Leu  Val  Ser
145                      150                      155                          160

Pro  Asp  Ser  Glu  Asn  Ile  Ile  Asp  Ile  Ser  His  Leu  Ser  Glu  Lys  Arg
                    165                          170                     175

Thr  Phe  Ile  Ser  Leu  Ala  Lys  Val  Ile  Gln  Asn  Ile  Ala  Asn  Gly  Ser
               180                      185                     190

Glu  Asn  Phe  Ser  Arg  Trp  Pro  Ala  Leu  Cys  Ser  Gln  Lys  Asp  Phe  Leu
          195                      200                     205

Lys  Glu  Cys  Ser  Asp  Arg  Ile  Phe  Arg  Phe  Leu  Ala  Glu  Leu  Cys  Arg
     210                      215                     220
```

( 2 ) INFORMATION FOR SEQ ID NO:7:

( i ) SEQUENCE CHARACTERISTICS:
        ( A ) LENGTH: 229 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Gln  Trp  Asp  Glu  Leu  Ala  Arg  Val  Leu  Val  Thr  Leu  Phe  Asp  Ser  Arg
1                    5                      10                          15

His  Leu  Leu  Tyr  Gln  Leu  Leu  Trp  Asn  Met  Phe  Ser  Lys  Glu  Val  Glu
               20                      25                      30

Leu  Ala  Asp  Ser  Met  Gln  Thr  Leu  Phe  Arg  Gly  Asn  Ser  Leu  Ala  Ser
          35                      40                      45

Lys  Ile  Met  Thr  Phe  Cys  Phe  Lys  Val  Tyr  Gly  Ala  Thr  Tyr  Leu  Gln
     50                      55                      60

Lys  Leu  Leu  Asp  Pro  Leu  Leu  Arg  Ile  Val  Ile  Thr  Ser  Ser  Asp  Trp
65                            70                      75                      80

Gln  His  Val  Ser  Phe  Glu  Val  Asp  Pro  Thr  Arg  Leu  Glu  Pro  Ser  Glu
               85                      90                      95

Ser  Leu  Glu  Glu  Asn  Gln  Arg  Asn  Leu  Leu  Gln  Met  Thr  Glu  Lys  Phe
                    100                     105                     110

Phe  His  Ala  Ile  Ile  Ser  Ser  Ser  Glu  Phe  Pro  Pro  Gln  Leu  Arg
          115                     120                     125

Ser  Val  Cys  His  Cys  Leu  Tyr  Gln  Val  Val  Ser  Gln  Arg  Phe  Pro  Gln
     130                     135                     140

Asn  Ser  Ile  Gly  Ala  Val  Gly  Ser  Ala  Met  Phe  Leu  Arg  Phe  Ile  Asn
145                      150                     155                          160

Pro  Ala  Ile  Val  Ser  Pro  Tyr  Glu  Ala  Gly  Ile  Leu  Asp  Lys  Lys  Pro
                    165                     170                     175

Pro  Pro  Arg  Ile  Glu  Arg  Gly  Leu  Lys  Leu  Met  Ser  Lys  Ile  Leu  Gln
               180                     185                     190
```

5,639,651

-continued

Ser Ile Ala Asn His Val Leu Phe Thr Lys Glu Glu His Met Arg Pro
        195                 200                 205

Phe Asn Asp Phe Val Lys Ser Asn Phe Asp Ala Ala Arg Arg Phe Phe
        210                 215                 220

Leu Asp Ile Ala Ser
225

( 2 ) INFORMATION FOR SEQ ID NO:8:

( i ) SEQUENCE CHARACTERISTICS:
        ( A ) LENGTH: 235 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Gly Lys Thr Glu Val Ala Gln Pro Leu Val Arg Leu Phe Thr His Thr
1               5                   10                  15

Glu Arg Ile Ala Pro Ile Ile Lys Ala Leu Ala Asp His Glu Ile Ser
        20                  25                  30

His Leu Thr Asp Pro Thr Thr Ile Phe Arg Gly Asn Thr Leu Val Ser
        35                  40                  45

Lys Met Met Asp Glu Ala Met Arg Leu Ser Gly Leu His Tyr Leu His
        50                  55                  60

Gln Thr Leu Arg Pro Val Leu Ser Gln Ile Val Ala Glu Lys Lys Pro
65                  70                  75                  80

Cys Glu Ile Asp Pro Ser Lys Ile Lys Asp Arg Ser Ala Val Asp Thr
                    85                  90                  95

Asn Leu His Asn Leu Gln Asp Tyr Val Glu Arg Val Phe Glu Ala Ile
                100                 105                 110

Thr Lys Ser Ala Asp Arg Cys Pro Lys Val Leu Cys Gln Ile Phe His
        115                 120                 125

Asp Leu Arg Glu Cys Ala Gly Glu His Phe Pro Ser Asn Arg Glu Val
        130                 135                 140

Arg Tyr Ser Val Val Ser Gly Phe Ile Phe Leu Arg Phe Phe Ala Pro
145                 150                 155                 160

Ala Ile Leu Gly Pro Lys Leu Phe Asp Leu Thr Thr Glu Arg Leu Asp
                    165                 170                 175

Ala Gln Thr Ser Arg Thr Leu Thr Leu Ile Ser Lys Thr Ile Gln Ser
                180                 185                 190

Leu Gly Asn Leu Val Ser Ser Arg Ser Ser Gln Gln Thr Cys Lys Glu
        195                 200                 205

Glu Phe Thr Val Glu Leu Tyr Lys Lys Phe Cys Thr Glu Gln His Val
        210                 215                 220

Asp Ala Val Lys His Phe Leu Glu Val Ile Ser
225                 230                 235

( 2 ) INFORMATION FOR SEQ ID NO:9:

( i ) SEQUENCE CHARACTERISTICS:
        ( A ) LENGTH: 229 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Asp Arg Thr Leu Leu Ala Ser Ile Leu Leu Arg Ile Phe Leu His Glu

|   |     |     |     |     |     |     |     |     |     |     |     |     |     |     |
|---|-----|-----|-----|-----|-----|-----|-----|-----|-----|-----|-----|-----|-----|-----|
| Lys | Leu | Glu | Ser<br>20 | Leu | Leu | Leu | Cys | Thr<br>25 | Leu | Asn | Asp | Arg | Glu<br>30 | Ile | Ser |
| Met | Glu | Asp<br>35 | Glu | Ala | Thr | Thr | Leu<br>40 | Phe | Arg | Ala | Thr | Thr<br>45 | Leu | Ala | Ser |
| Thr | Leu<br>50 | Met | Glu | Gln | Tyr | Met<br>55 | Lys | Ala | Thr | Ala | Thr<br>60 | Gln | Phe | Val | His |
| His<br>65 | Ala | Leu | Lys | Asp | Ser<br>70 | Ile | Leu | Lys | Ile | Met<br>75 | Glu | Ser | Lys | Gln | Ser<br>80 |
| Cys | Glu | Leu | Ser | Pro<br>85 | Ser | Lys | Leu | Glu | Lys<br>90 | Asn | Glu | Asp | Val | Asn<br>95 | Thr |
| Asn | Leu | Thr | His<br>100 | Leu | Leu | Asn | Ile | Leu<br>105 | Ser | Glu | Leu | Val | Glu<br>110 | Lys | Ile |
| Phe | Met | Ala<br>115 | Ser | Glu | Ile | Leu | Pro<br>120 | Pro | Thr | Leu | Arg | Tyr<br>125 | Ile | Tyr | Gly |
| Cys | Leu<br>130 | Gln | Lys | Ser | Val | Gln<br>135 | His | Lys | Trp | Pro | Thr<br>140 | Asn | Thr | Thr | Met |
| Arg<br>145 | Thr | Arg | Val | Val | Ser<br>150 | Gly | Phe | Val | Phe | Leu<br>155 | Arg | Leu | Ile | Cys | Pro<br>160 |
| Ala | Ile | Leu | Asn | Pro<br>165 | Arg | Met | Phe | Asn | Ile<br>170 | Ile | Ser | Asp | Ser | Pro<br>175 | Ser |
| Pro | Ile | Ala | Ala<br>180 | Arg | Thr | Leu | Ile | Leu<br>185 | Val | Ala | Lys | Ser | Val<br>190 | Gln | Asn |
| Leu | Ala | Asn<br>195 | Leu | Val | Glu | Phe | Gly<br>200 | Ala | Lys | Glu | Pro | Tyr<br>205 | Met | Glu | Gly |
| Val | Asn<br>210 | Pro | Phe | Ile | Lys | Ser<br>215 | Asn | Lys | His | Arg | Met<br>220 | Ile | Met | Phe | Leu |
| Asp<br>225 | Glu | Leu | Gly | Asn |     |     |     |     |     |     |     |     |     |     |     |

( 2 ) INFORMATION FOR SEQ ID NO:10:

( i ) SEQUENCE CHARACTERISTICS:
        ( A ) LENGTH: 234 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

|   |     |     |     |     |     |     |     |     |     |     |     |     |     |     |
|---|-----|-----|-----|-----|-----|-----|-----|-----|-----|-----|-----|-----|-----|-----|
| Arg<br>1 | Ile | Glu | Glu | Trp<br>5 | Phe | His | Val | Leu | Ile<br>10 | Asp | Lys | Glu | Leu | Ala<br>15 | Lys |
| Ile | Asp | Gly | Thr<br>20 | Val | Ser | Arg | Ile | Asn<br>25 | Gln | Lys | Asn | Leu | Asp<br>30 | Ser | Lys |
| His | Val | Phe<br>35 | Asn | Ser | Leu | Phe | Arg<br>40 | Gly | Asn | Ser | Ile | Leu<br>45 | Thr | Lys | Ser |
| Ile | Glu<br>50 | Gln | Tyr | Phe | Phe | Arg<br>55 | Val | Gly | Asn | Glu | Tyr<br>60 | Leu | Ser | Lys | Ala |
| Leu<br>65 | Ser | Ala | Ile | Leu | Lys<br>70 | Glu | Ile | Ile | Glu | Ser<br>75 | Asn | Lys | Ser | Cys | Glu<br>80 |
| Leu | Asp | Pro | Ala | Arg<br>85 | Val | Lys | Glu | Lys | Asp<br>90 | Glu | Val | Lys | Lys | Arg<br>95 | Lys |
| Ile | Ile | Ala | Asp<br>100 | Asn | Tyr | Lys | Arg | Leu<br>105 | Tyr | Ser | Trp | Val | Thr<br>110 | Lys | Ile |
| Trp | Lys<br>115 | Arg | Leu | Tyr | Ala | Thr<br>120 | Ser | Asn | Asp | Leu | Pro<br>125 | Ile | Glu | Ile | Arg |

```
Asn Val Leu Lys Ile Phe Arg Gln Lys Leu Glu Ile Ile Cys Ile Asp
    130             135             140

Asp Thr Leu Gln Ile Ile Leu Asn Gly Ile Ser Gly Leu Leu Phe Leu
145             150             155                         160

Arg Phe Phe Cys Pro Val Ile Leu Asn Pro Lys Leu Phe Lys Tyr Val
                165             170             175

Ser Gln Asn Leu Asn Glu Thr Ala Arg Arg Asn Leu Thr Leu Ile Ser
            180             185             190

Lys Val Leu Leu Asn Leu Ser Thr Leu Thr Gln Phe Ala Asn Lys Glu
        195             200             205

Pro Trp Leu Met Lys Met Asn Asn Phe Ile Asp Lys Arg His Asn Asp
    210             215             220

Leu Leu Asp Tyr Ile Asp Lys Met Thr Gln
225             230
```

( 2 ) INFORMATION FOR SEQ ID NO:11:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

```
Leu Ala Gln Leu Ile Thr Arg Thr Gln Ala Arg Cys Arg Gly Phe Leu
1               5               10              15

Met Arg Val Glu Phe Lys Lys Met Met Glu Arg Arg Glu Cys
            20              25              30
```

( 2 ) INFORMATION FOR SEQ ID NO:12:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

```
Asn Glu Gly Leu Ile Thr Arg Leu Gln Ala Arg Cys Arg Gly Tyr Leu
1               5               10              15

Val Arg Gln Glu Phe Arg Ser Arg Met Asn Phe Leu Lys Lys
            20              25              30
```

( 2 ) INFORMATION FOR SEQ ID NO:13:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

```
Gln Ile Pro Ala Ile Thr Cys Ile Gln Ser Gln Trp Arg Gly Tyr Lys
1               5               10              15

Gln Lys Lys Ala Tyr Gln Asp Arg Leu Ala Tyr Leu Arg Ser
            20              25              30
```

( 2 ) INFORMATION FOR SEQ ID NO:14:

( i ) SEQUENCE CHARACTERISTICS:
        ( A ) LENGTH: 30 amino acids (B) TYPE: amino acid
(D) TOPOLOGY: linear (ii) MOLECULE TYPE: peptide (xi) SEQUENCE DESCRIPTION: SEQ ID NO:14:

His Lys Asp Glu Val Val Lys Ile Gln Ser Leu Ala Arg Met His Gln
1               5                   10                  15
Ala Arg Lys Arg Tyr Arg Asp Arg Leu Gln Tyr Phe Arg Asp
            20                  25                  30

(2) INFORMATION FOR SEQ ID NO:15:

(i) SEQUENCE CHARACTERISTICS:
    (A) LENGTH: 30 amino acids
    (B) TYPE: amino acid
    (D) TOPOLOGY: linear (ii) MOLECULE TYPE: peptide (xi) SEQUENCE DESCRIPTION: SEQ ID NO:15:

His Ile Asn Asp Ile Ile Lys Ile Gln Ala Phe Ile Arg Ala Asn Lys
1               5                   10                  15
Ala Arg Asp Asp Tyr Lys Thr Leu Ile Asn Ala Glu Asp Pro
            20                  25                  30

(2) INFORMATION FOR SEQ ID NO:16:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO:16:

Ile Xaa Xaa Ile Gln Xaa Xaa Xaa Arg Xaa Xaa Xaa Xaa Arg Xaa Xaa
1               5                   10                  15
Tyr Xaa Xaa Arg
            20

(2) INFORMATION FOR SEQ ID NO:17:

(i) SEQUENCE CHARACTERISTICS:
    (A) LENGTH: 59 amino acids
    (B) TYPE: amino acid
    (D) TOPOLOGY: linear (ii) MOLECULE TYPE: peptide (xi) SEQUENCE DESCRIPTION: SEQ ID NO:17:

Ala Leu His Ala Ala Val Ile Ala Ile Asn Glu Ala Ile Asp Arg Arg
1               5                   10                  15
Ile Pro Ala Asp Thr Phe Ala Ala Leu Lys Asn Pro Asn Ala Met Leu
            20                  25                  30
Val Asn Leu Glu Glu Pro Leu Ala Ser Thr Tyr Gln Asp Ile Leu Tyr
            35                  40                  45
Gln Ala Lys Gln Asp Lys Met Thr Asn Ala Lys
        50                  55

(2) INFORMATION FOR SEQ ID NO:18:

(i) SEQUENCE CHARACTERISTICS:
    (A) LENGTH: 59 amino acids
    (B) TYPE: amino acid
    (D) TOPOLOGY: linear ( i i ) MOLECULE TYPE: peptide ( x i ) SEQUENCE DESCRIPTION: SEQ ID NO:18:

| Asn | Thr | Phe | Ser | Ala | Leu | Ala | Asn | Ile | Asp | Leu | Ala | Leu | Glu | Gln | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Ala | Leu | Ala | Leu | Phe | Arg | Ala | Leu | Gln | Ser | Pro | Ala | Leu | Gly | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Arg | Gly | Leu | Gln | Gln | Gln | Asn | Ser | Asp | Trp | Tyr | Leu | Lys | Gln | Leu | Leu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Ser | Asp | Lys | Gln | Gln | Lys | Arg | Gln | Ser | Gly | Gln |
|-----|-----|-----|-----|-----|-----|-----|-----|-----|-----|-----|
|     | 50  |     |     |     |     | 55  |     |     |     |     |

( 2 ) INFORMATION FOR SEQ ID NO:19:

( i ) SEQUENCE CHARACTERISTICS:
        ( A ) LENGTH: 59 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

| Arg | Arg | Leu | Ala | Ala | Val | Ala | Leu | Ile | Asn | Ala | Ala | Ile | Gln | Lys | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Ala | Glu | Lys | Thr | Val | Leu | Glu | Leu | Met | Asn | Pro | Glu | Ala | Gln | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Pro | Gln | Val | Tyr | Pro | Phe | Ala | Ala | Asp | Leu | Tyr | Gln | Lys | Glu | Leu | Ala |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Thr | Leu | Gln | Arg | Gln | Ser | Pro | Glu | His | Asn | Leu |
|-----|-----|-----|-----|-----|-----|-----|-----|-----|-----|-----|
|     | 50  |     |     |     |     | 55  |     |     |     |     |

( 2 ) INFORMATION FOR SEQ ID NO:20:

( i ) SEQUENCE CHARACTERISTICS:
        ( A ) LENGTH: 59 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

| Glu | Met | Leu | Ser | Ser | Val | Ala | Leu | Ile | Asn | Arg | Ala | Leu | Glu | Ser | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Asp | Val | Asn | Thr | Val | Trp | Lys | Gln | Leu | Ser | Ser | Ser | Val | Thr | Gly | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Asn | Ile | Glu | Glu | Glu | Asn | Cys | Gln | Arg | Tyr | Leu | Asp | Glu | Leu | Met |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Lys | Leu | Lys | Ala | Gln | Ala | His | Ala | Glu | Asn | Asn |
|-----|-----|-----|-----|-----|-----|-----|-----|-----|-----|-----|
|     | 50  |     |     |     |     | 55  |     |     |     |     |

( 2 ) INFORMATION FOR SEQ ID NO:21:

( i ) SEQUENCE CHARACTERISTICS:
        ( A ) LENGTH: 59 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

| Glu | Arg | Ile | Leu | Ala | Ile | Gly | Leu | Ile | Asn | Glu | Ala | Leu | Asp | Glu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

```
Asp Ala Gln Lys Thr Leu Gln Ala Leu Gln Ile Pro Ala Ala Lys Leu
            20                  25                  30
Glu Gly Val Leu Ala Glu Val Ala Gln His Tyr Gln Asp Thr Leu Ile
            35                  40                  45
Arg Ala Lys Arg Glu Lys Ala Gln Glu Ile Gln
            50                  55
```

( 2 ) INFORMATION FOR SEQ ID NO:22:

( i ) SEQUENCE CHARACTERISTICS:
        ( A ) LENGTH: 59 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

```
Lys Phe Ala Leu Gly Ile Phe Ala Ile Asn Glu Ala Val Glu Ser Gly
1                   5                   10                  15
Asp Val Gly Lys Thr Leu Ser Ala Leu Arg Ser Pro Asp Val Gly Leu
            20                  25                  30
Tyr Gly Val Ile Pro Glu Cys Gly Glu Thr Tyr His Ser Asp Leu Ala
            35                  40                  45
Glu Ala Lys Lys Lys Lys Leu Ala Val Gly Asp
            50                  55
```

( 2 ) INFORMATION FOR SEQ ID NO:23:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

```
Ala Ile Asn Ala Gly Asp Leu Pro Leu Tyr Leu Lys
1                   5                   10
```

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:24:

CCCMGVTGTG GMGTKCCHGA                                            20

( 2 ) INFORMATION FOR SEQ ID NO:25:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:25:

CCCAGVRMRT GGCCAADTTC ATG                                        23

( 2 ) INFORMATION FOR SEQ ID NO:26:

(i) SEQUENCE CHARACTERISTICS:
    (A) LENGTH: 14 base pairs
    (B) TYPE: amino acid
    (D) TOPOLOGY: linear (ii) MOLECULE TYPE: peptide (xi) SEQUENCE DESCRIPTION: SEQ ID NO:26:

```
Ile Xaa Xaa Ile Gln Xaa Xaa Xaa Arg Xaa Xaa Xaa Xaa Arg
 1           5                   10
```

GAP-RELATED GENE, HUMAN IQGAP1

This invention was made with Government support under grant number R1AR16265 awarded by the National Institutes of Health. The Government has certain rights in the invention.

BACKGROUND OF THE INVENTION

The field of the invention is tumor suppression.

The mechanisms of tumorigenesis in vivo are poorly understood. Overwhelming evidence indicates that specific mutated forms of the $p21^{ras}$ gene (ras) contribute to tumorigenesis (Barbacid, M., 1987, Ann. Rev. Biochem., 56:779–827). When analyzed in a variety of neoplasms, the ras genes frequently contain characteristic point mutations that result in constitutive activation of $p21^{ras}$ (Barbacid, M., 1987, Ann. Rev. Biochem. 56:779–827; Bourne, H. R. et al., 1990, Nature 348:125–132). Expression of abnormally high levels of normal $p21^{ras}$ as a result of gene amplification or regulatory sequence mutations may also contribute to the transformation of normal cells to cancerous cells.

The ras genes which encode 21 kDa proteins are expressed ubiquitously and are found associated with the plasma membrane in the cytoplasm of the cell (Barbacid, M., 1987, Ann. Rev. Biochem. 56:779–827). $p21^{ras}$ is a guanine nucleotide-binding protein which catalyzes the hydrolysis of bound guanine triphosphate (GTP) to guanine diphosphate (GDP) (Barbacid, M., 1987, Ann. Rev. Biochem. 56:779–827; Bourne, H. R. et al., 1990, Nature, 348:125–132; Bourne, H. R. et al., 1991, Nature, 349:117–127) and is believed to be a key component of a complex intracellular signal transduction pathway from the plasma membrane to the nucleus. It is active when bound to GTP and inactive in its GDP-bound state.

Other proteins may be associated with $p21^{ras}$. Such accessory proteins, such as mammalian GTPase activating protein (GAP or p120-GAP) and neurofibromin (NF1-GAP), the product of the neurofibromatosis type 1 gene locus (Trahey, M. et al., 1987, Science, 238:542–545; Trahey, M. et al., 1988, Science, 242:1697–1700; Vogel, U.S. et al., 1988, Nature, 335:90–93; Martin, G. A. et al., 1990, Cell, 63:843–849; Ballester, R. et al., 1990, Cell, 63:851–859), stimulate guanine nucleotide exchange as well as the intrinsic GTPase activity of p21ras (Bourne, H. R. et al., 1990, Nature 348:125–132). These proteins are collectively referred to as ras-GAPs.

In neurofibromatosis (NF type 1), an autosomal dominant disease characterized by various clinical disorders, including benign neurofibromas, constitutively-active $p21^{ras}$ has been attributed to nonfunctional neurofibromin (Basu, T. N. et al., 1992, Nature, 356:713–715; Li, Y. et al., 1992, Cell 69:275–281). Certain tumors unrelated to neurofibromatosis have also been found to contain mutated neurofibromin lacking GAP activity (Yatani, A. et al., 1990, Cell, 61:769–776).

The ras gene is the most frequently identified oncogene in human cancer, but oncogenic $p21^{ras}$ is resistant to the action of known mammalian ras-GAPs (Trahey, M. et al., 1987, Science, 238:542–545; Vogel, U.S. et al., 1988, Nature, 335:90–93).

SUMMARY OF THE INVENTION

The invention is based on the discovery of a gene which encodes a novel GAP protein. This protein, designated IQGAP1, can be used as a tumor suppressor to reduce oncogenic ras activity that may be resistant to other known mammalian ras-GAPs. The invention provides compositions and methods to treat a large class of tumors characterized by a defect in $p21^{ras}$ expression or activity. Since ras is central to many receptor-mediated cell signalling pathways, IQGAP1 can also be used to manipulate intracellular signal transduction and cell proliferation.

The invention features a substantially pure nucleic acid, the sequence of which encodes IQGAP1. The invention also includes a substantially pure nucleic acid the sequence of which hybridizes to a nucleic acid encoding IQGAP1. In one embodiment, the nucleic acid sequence includes a sequence substantially identical to the sequence of SEQ ID NO:2, as shown in FIG. 1. By "hybridizes" is meant binds to or associates with a nucleic acid of specified sequence. By the term "high stringency" is meant DNA hybridization and wash conditions characterized by relatively high temperature and low salt concentration, e.g., conditions described in Sambrook et al., 1989, Molecular Cloning: a Laboratory Manual, second edition, Cold Spring Harbor Press, Cold Spring Harbor, N.Y., e.g., 0.2× SSC, 0.1% SDS at 60° C. wash conditions. A "substantially pure nucleic acid", as used herein, refers to a nucleic acid sequence, segment, or fragment which has been purified from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA, which have been purified from proteins which naturally accompany it in the cell. In another embodiment, the nucleic acid includes a sequence which encodes a protein or polypeptide having the amino acid sequence of SEQ ID NO:1, as shown in FIG. 2B. Degenerate variants of the nucleic acid encoding IQGAP1 are also within the invention. Degenerate variants are nucleic acids which encode a polypeptide with the amino acid sequence of SEQ ID NO:1, but differ in nucleotide sequence from the sequence given in SEQ ID NO:2.

In a related aspect, the invention includes a cell comprising the nucleic acid which encodes IQGAP1, and such a cell which expresses the IQGAP1 gene product. In one embodiment, the invention includes a substantially pure IQGAP1 polypeptide which includes the amino acid sequence of SEQ ID NO:1. As used herein, the term "substantially pure" describes a protein or polypeptide, which has been separated from components which naturally accompany it. Typically, a protein or polypeptide is substantially pure when at least 10%, more preferably at least 20%, more preferably at least 50%, more preferably at least 60%, more preferably at least 75%, more preferably at least 90%, and most preferably at least 99%, of the total material (by volume, by wet or dry weight, or by mole per cent or mole fraction) in a sample is the protein or polypeptide of interest. Purity can be measured by any appropriate method, e.g., in the case of polypeptides by column chromatography, polyacrylamide gel electrophoresis, or high pressure liquid chromatographic (HPLC) analysis. In another embodiment, the polypeptide contains one or more copies of an IQ motif. An "IQ motif" is defined as an amino acid sequence of 20–40 amino acids in length containing an isoleucine residue (designated "I") immediately followed by a glutamine residue (designated "Q") which has at least 50% sequence similarity to the consensus sequence IXXIQXXXRXXXXR (SEQ ID NO:26). Amino acid sequences that contain an IQ motif are shown in FIG. 3C.

The invention also includes a biologically active fragment of IQGAP1. By the term "biologically active" is meant having the ability to bind p21$^{ras}$ or reduce the activity of p21$^{ras}$. The biologically active fragment of IQGAP1 preferably contains the GAP catalytic domain of the protein, i.e., SEQ ID NO:3. Putative biologically active fragments of IQGAP1 can be generated by methods known to those skilled in the art.

As used herein, the term "fragment or segment", as applied to a polypeptide, will ordinarily be at least about 5 contiguous amino acids, typically at least about 10 contiguous amino acids, more typically at least about 20 contiguous amino acids, usually at least about 30 contiguous amino acids, preferably at least about 40 contiguous amino acids, more preferably at least about 50 contiguous amino acids, and most preferably at least about 60 to 80 or more contiguous amino acids in length. Such peptides can be generated by methods known to those skilled in the art, including proteolytic cleavage of the protein, de novo synthesis of the fragment, or genetic engineering.

In another aspect, the invention features an antibody which specifically binds to IQGAP1.

In yet another aspect, the invention features a method of detecting a neoplastic cell in a tissue. The method involves measuring IQGAP1 expression wherein decreased expression of the gene product compared to a standard or known level of expression associated with normal tissue is indicative of the presence of a neoplastic cell. In one embodiment, gene expression is measured by isolating RNA from a tissue, and measuring the amount of IQGAP1 RNA or cDNA. In another embodiment, gene expression is measured by isolating protein from a tissue, contacting the protein with the IQGAP1-specific antibody of the invention, and measuring binding of the antibody. A decrease in the level of IQGAP1 protein compared to a standard or known level associated with normal tissue as measured by the binding of IQGAP1-specific antibody is indicative of a neoplastic cell.

The invention also includes a method of diagnosing cancer, i.e., detecting a neoplastic cell in a tissue, by testing for the presence of a mutation in the IQGAP1 gene. The mutation may be a point mutation, translocation, deletion, rearrangement or any other aberration in the sequence compared to the wild type IQGAP1 DNA sequence. Mutations may be detected by known methods, such as Southern blotting, DNA sequencing, polymerase chain reaction (PCR) or in situ hybridization. Mutations may also affect protein expression, and thus, can be identified using techniques that detect an aberrant increase or decrease in protein expression, e.g., Northern blotting or Western blotting. The presence of an IQGAP1 gene mutation in a tissue sample indicates that a neoplastic cell is present in the tissue tested.

The invention also features a method of treating cancer in a mammal by administering a IQGAP1 polypeptide (or a biologically active fragment thereof) or IQGAP1 nucleic acid to reduce the activity of p21$^{ras}$.

DETAILED DESCRIPTION

The drawings are first briefly described.

Drawings FIG. 1 is a DNA sequence (SEQ ID NO:2) of the human IQGAP1 gene.

FIG. 2A is diagram which shows the major open reading frame of IQGAP1 cDNA as a shaded box. The cDNA also includes 468 bp of 5' and 2135 bp of 3' untranslated region. The putative start codon of IQGAP1 is preceded by an in frame stop codon (indicated by an asterisk).

FIG. 2B is an amino acid sequence of the human IQGAP1 protein (SEQ ID NO:1). The 3' untranslated segment ends in a short oligo(A) sequence immediately downstream of a standard poly(A) addition signal. The putative GAP catalytic domain in the protein sequence is boxed. The six upstream repeats are indicated by solid arrows; the four tandem IQ motifs by shaded arrows.

FIG. 3A is a diagram showing location of MP20 homologous region, N-terminal repeats, IQ motifs, and the GAP-related domain (GRD). Protein segments of approximately 150 amino acids upstream and 350 amino acids downstream of the GRD of IQGAP1 show 23% sequence identity (48% similarity) to the corresponding segments of the yeast sar1 protein (Wang, Y. et al., Cell Regulation 2:453–465; Imai, Y., Mizake, S., Hughes, D. A., and Yamamoto, M., 1991, Mol. Cell. Biol. 11: 3088–3094). The GRD of the two proteins are 27% identical (54% similar).

FIG. 3B is a sequence alignment of the putative catalytic domains of all known rasGAP-like proteins generated by the PILEUP program (Genetics Computer Group, University of Wisconsin). Amino acid residues that are conserved in at least 6 of the 8 proteins are indicated with plus (+) signs. Exclamation marks (!) indicate conservative substitutions.

FIG. 3C is an alignment of the four IQ motifs in IQGAP1. A consensus sequence is shown below the alignment. Residues that are conserved in at least 3 of the IQ motifs are indicated with plus (+) signs). Exclamation marks (!) indicate positions where only conservative substitutions are found. The high level of sequence identity between the first IQ motif of IQGAP1 and a region of chicken myosin (Ch.M) heavy chain implicated in essential light chain binding is also shown.

FIG. 3D is an alignment of the six N-terminal protein repeat domains in IQGAP1. A consensus sequence is shown below the alignment. Residues that are conserved in at least 5 of the N-terminal repeats are indicated with plus (+) signs). Exclamation marks (!) indicate positions where only conservative substitutions are found.

Figure 5:
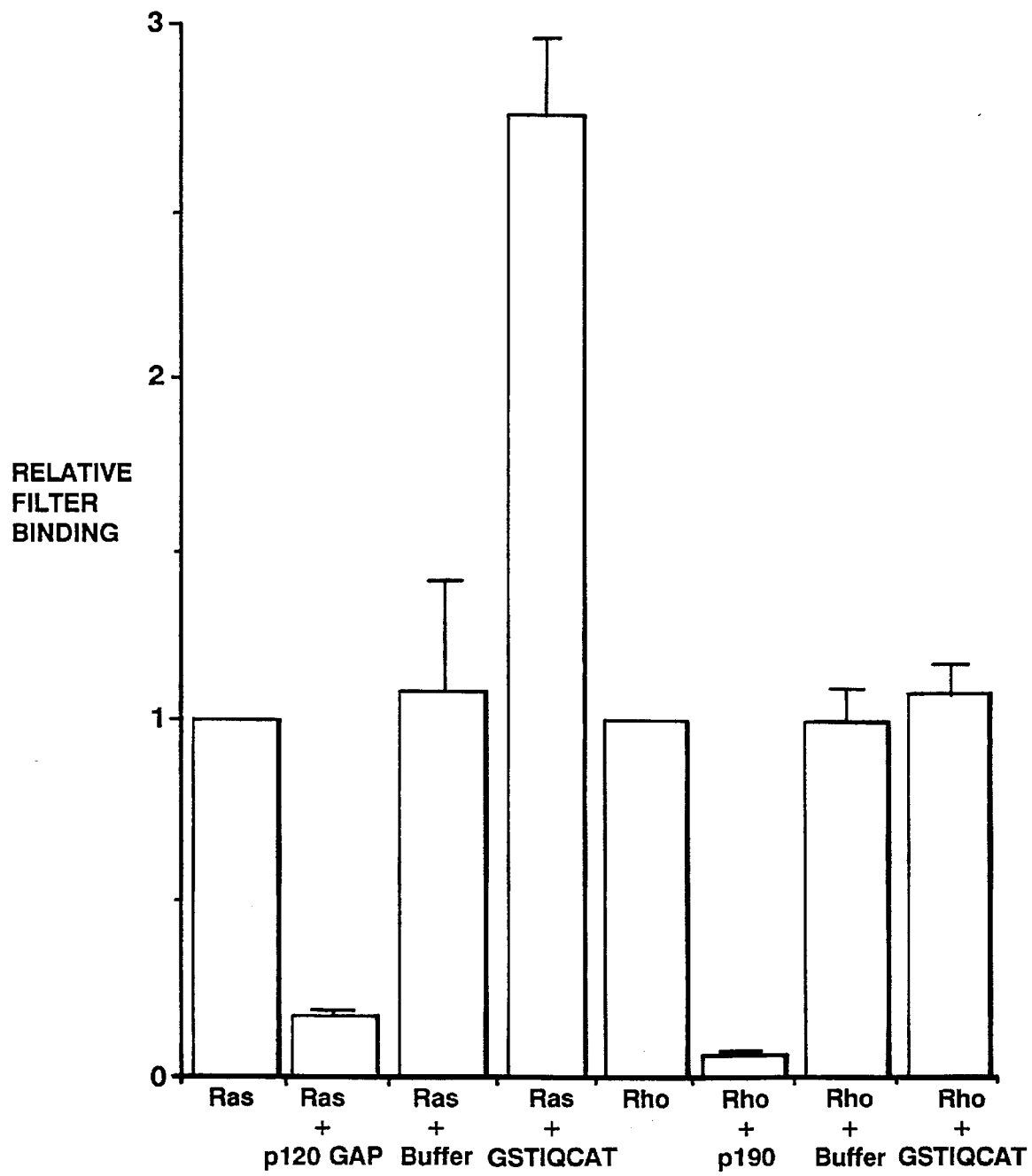

FIG. 5 is a bar graph showing the results of a filter binding assay in which GTP-loaded Ras or Rho were tested as substrates for p120 Ras-GAP, p190 RhoGAP, or GSTIQ-CAT. Values were normalized to amounts detected with Ras or Rho alone. Each value represents the average of at least six independent assays.

CLONING OF IQGAP1

DNA manipulations were performed according to procedures well known in the art (Sambrook, J., Fritsch, E. F., and Maniatis, T., 1989, Molecular Cloning: A Laboratory Manual, 2$^{nd}$ ed. Cold Spring Harbor Laboratory, Cold Spring Harbor, N.Y.). An initial IQGAP1 DNA probe was generated by RNA-PCR using total RNA from human metastatic osteosarcoma tissue and employing degenerate oligonucleotide primers (sense primer:

5'CCC(A,C)G(A,C,G)TGTGG(A,C)GT(G,T)CC(A,T,C)GA (SEQ ID NO:24); antisense primer:

5'CCCAG(A,G,C) (A,G) (A,C) (A,G)TGGCCAA(A,G,T)TTCATG (SEQ ID NO:25) corresponding to conserved peptides in matrix metalloproteinases (Woessner, J. F., 1991, FASEB J. 5:2145–2154), a gene family unrelated to rasGAPs. Routine procedures known in the art were used to isolate total RNA using guanidinium-thiocyanate-phenol procedure well known in the art, and RNA-PCR was carried out according to known methods.

Additional human IQGAP1 cDNAs were isolated from oligo(dT)-primed placental and randomly-primed liver cDNA libraries (Clontech, Palo Alto, Calif), and from a pre-B lymphocyte cDNA library. Mouse IQGAP1 cDNAs were isolated from a murine pre-B cell library. The sequence of IQGAP1 cDNA was determined on both strands by the dideoxychain termination technique (SEQUENASE® enzyme, United States Biochemicals, Cleveland, Ohio), using multiple cDNA suones and subclones.

Expression of IQGAP1

For the purpose of evaluating IQGAP1 expression, standard protocols can be followed for Northern analyses, utilizing a radioactively-labeled IQGAP1 single-strand cDNA probe generated by standard methods (Sambrook, J. et al., 1989, Cold Spring Harbor Laboratory, Cold Spring Harbor, N.Y.; Saiki, R. K. et al., 1988, Science, 239:487–491).

IQGAP1 mRNA expression was analyzed using a multiple tissue RNA blot (Clontech, Palo Alto, Calif), containing size-fractionated poly(A) RNA from normal human tissues. The blot was probed using standard high stringency conditions with a randomly-primed 1100 bp cDNA fragment encompassing the putative catalytic domain of IQGAP1.

Figure 4A:
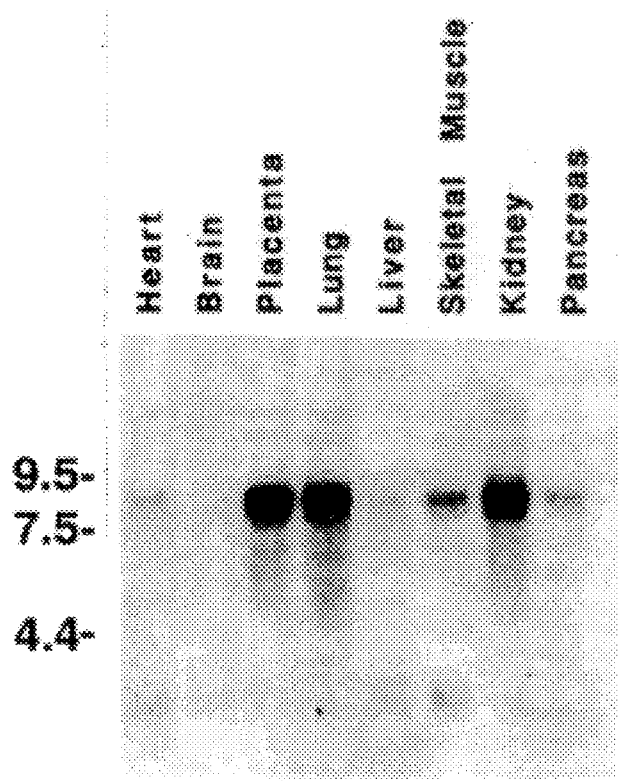
FIG. 4A is a photograph of a Northern blot showing IQGAP1 mRNA expression in normal human tissues. The RNA blot was hybridized with an IQGAP1.
Figure 4B:
FIG. 4B is a photograph of a Northern blot. The RNA blot was hybridized with a human NF1 cDNA probe as a control.

To determine the tissue distribution of IQGAP1 expression, RNA blot analysis was performed using the cloned cDNA as probe (FIG. 4A). A closely spaced mRNA doublet of 7.5–8.0 kb in length was detected in all tissues examined, although the RNA levels differed significantly between tissues. The highest mRNA levels were detected in placenta, lung, and kidney. Much lower levels were seen in heart, liver, skeletal muscle, and pancreas, and IQGAP1 mRNA was not detectable in brain. While ras proteins are expressed ubiquitously, the restricted tissue expression of IQGAP1 suggests that it may function in ras pathways that are specific to particular cell types.

Characterization of IQGAP1

Figure 2A:
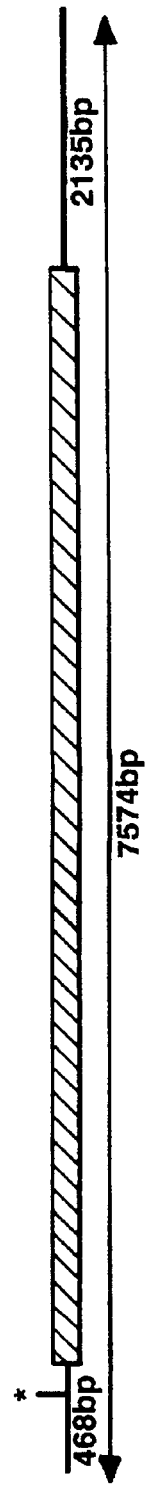

Using a RNA-PCR method to identify members of the matrix metalloproteinase gene family expressed in tumor tissue, a 600 bp PCR product was isolated. The nucleotide sequence of this PCR product predicted a protein having significant homology to the catalytic region of rasGAPs. Using this PCR fragment as a probe, several overlapping cDNAs from three human cDNA libraries were isolated. A contiguous sequence of 7574 bp was identified. This sequence contained a single major open reading frame predicting a protein of 1657 amino acids with a calculated molecular weight of 189,261 daltons (FIGS. 2A and 2B). The predicted protein, designated IQGAP1, exhibits substantial sequence similarity to the catalytic domain of all previously reported rasGAPs, particularly at amino acid positions that are well conserved amongst the other GAPs (FIG. 3B).

"Homology", as used herein, refers to the subunit sequence similarity between two polymeric molecules, e.g., between two nucleic acid molecules, e.g., two DNA molecules, or two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., 5 positions in a polymer 10 subunits in length), of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC'5 and 3'TATGGC'5 share 50% homology.

Although most amino acids that are invariant between previously analyzed rasGAPs are also present in IQGAP1, there are some exceptions. Most notably, IQGAP1 contains two tandem tyrosine residues (amino acids 1192 and 1193), instead of the phenylalanine-leucine residues seen in all other rasGAPs. Mutation of the invariant leucine to an isoleucine in p120GAP results in a protein that binds ras but is unable to promote its GTPase activity (Brownbridge, G. G., et al., 1993, J. Biol. Chem. 268:10914–10919), suggesting that IQGAP1 interacts with ras proteins without promoting their GTPase activity. Another difference between IQGAP1 and other rasGAPs is seen at Thr1146, which is an arginine in all other rasGAPs. To further analyze these amino acid sequence differences, several mouse IQGAP1 cDNAs were also studied. The putative catalytic domains of mouse and human IQGAP1 were found to differ in only three residues, at positions that are not conserved in the other rasGAPs.

Figure 3A:
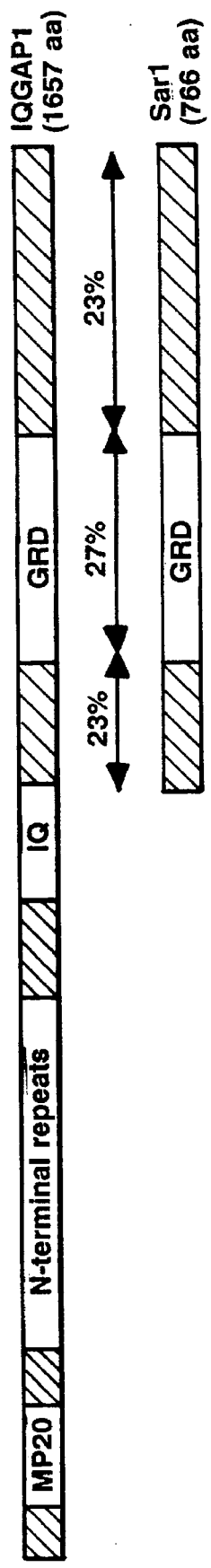

IQGAP1 is most closely related to the S.pombe rasGAP sar1, both in the putative catalytic domain and in sar1 sequences outside of this domain (FIG. 3A). IQGAP1 and S. pombe sar1 share 27% amino acid sequence identity (aligned identical amino acids/total amino acids) in their putative catalytic domains and are 54% amino acid similarity (aligned amino acids which are either identical or conservatively related in structure/total amino acids) in this region. There are also spacing features in this region that are unique to IQGAP1 and sar1, and are not seen in the other rasGAPs. The sequence similarity between IQGAP1 and sar1 extends beyond the putative catalytic domain, and includes the entire sar1 protein, with an overall sequence identity of 23% between the proteins. The similarity extends to the extreme C-termini of the two proteins, which end in FYGK (IQGAP1) and FLRK (sar1).

Sar1-deficient S. pombe mutants have a phenotype similar to that of yeast harboring activated ras alleles but, there is no evidence that sar1 plays a role as an effector of ras function in S. pombe (Wang, Y. et al., Cell Regulation 2:453–465; Imai, Y., Mizake, S., Hughes, D. A., and Yamamoto, M., 1991, Mol. Cell. Biol. 11: 3088–3094). Since sar1 plays appears to play an exclusively negative regulatory function in yeast, it is likely that IQGAP1 functions analogously in mammals. The observation that mutational activation of ras contributes to a substantial fraction of human tumors suggest that IQGAP1 can function as a tumor suppressor. The absence of IQGAP1 in cells could lead to increased ras activity.

No significant homology was detected between the IQGAP1 polypeptide and the p120-GAP. Regions outside of the catalytic domain of sar1 are clearly distinct in terms of sequence and arrangement when compared to the characterized mammalian ras-GAPs. These data suggest that IQGAP1 is the mammalian homolog of the yeast sar1 proteins and a novel member of the mammalian rasGAP family.

The presence of a domain in IQGAP1 that resembles the rasGAP catalytic domain found in p120 rasGAP and neurofibromin suggests that this domain could interact specifically with ras family GTPases and potentially promote hydrolysis of GTP by ras. To test this possibility, a bacterial fusion protein was prepared that contains the putative catalytic domain of IQGAP1 linked to a glutathione-S-transferase polypeptide (GST-IQCAT) for analysis of GAP activity. The GST-IQCAT plasmid was prepared by subcloning a 1.8 kb fragment of IQGAP1 encompassing the complete GAP-related domain into the bacterial vector GEX-2. Purification of the expressed fusion protein and assay of GAP activity in a filter binding assay were carried out using known methods (Settleman, J., Albright, C. F., Foster, L., and Weinberg, R. A., 1992, Nature 359:153–154). Expression and purification of the fusion protein were confirmed using SDS-PAGE.

GAP activity was tested using [γ32P]-GTP-loaded Ras or Rho proteins produced in bacteria as substrates. GTP-loaded Ras or Rho were incubated for 10 minutes with either a buffer control, 500 ng of GST-IQCAT, purified p120 rasGAP, or p190 rhoGAP; GTP hydrolysis was determined in a filter binding assay. Positive controls that included Ras plus p120 RasGAP, and Rho plus p190 rhoGAP demonstrated GAP-promoted hydrolysis indicating that the purified GTPases were capable of interacting with their respective GAPs (FIG. 5). In contrast, GST-IQCAT failed to promote hydrolysis of GTP by Ras. Incubation of the filters with GST-IQCAT consistently resulted in an increase in the retention of ras (but not rho) on the filters. These data suggest that GST-IQCAT can specifically bind ras and interact with ras in a manner that does not invoke the catalytic activity of ras.

Genomic localization of the IQGAP1 gene

To map the chromosomal localization of the IQGAP1 gene, a randomly-primed 1100 bp cDNA fragment containing the catalytic domain of IQGAP1 was used to hybridize blots containing EcoRI-digested DNAs representing a panel of rodent-human somatic cell hybrids.

Analysis of a panel of 43 rodent-human somatic cell hybrids containing defined overlapping subsets of human chromosome with a catalytic domain cDNA probe revealed specific human IQGAP1 restriction fragments only in hybrids containing human chromosome 15.

To confirm the location of the gene, two additional hybrids containing both partners of a X;15 translocation were analyzed. This experiment confirmed the original localization and allowed the sublocalization of IQGAP1 to chromosome 15 p or the proximal region of 15 q. Although this region of chromosome 15 does not harbor any known tumor suppressor genes, recurrent translocations affecting this region have been detected in both lung and renal cancers (Presti, J. C. et al., 1991, Cancer Res. 51:1544–1552; Zhou, J. et al., 1993, Cancer Genet. Cytogenet. 69: 1–6).

IQ motifs

In addition to the putative catalytic domain of IQGAP1, the protein contains three other noteworthy features. A region of IQGAP1 from amino acids 48–161 exhibits 29% sequence identity to the Drosophila muscle protein MP-20 (FIG. 3A). MP-20 is a 20 kDa muscle-specific putative calcium-binding protein of unknown function (Ayme-Southgate, A. et al., 1989, J. Cell Biol. 108:521–531).

The IQGAP1 protein sequence was also found to contain four tandemly repeated (30 amino acid spacing) so-called "IQ" motifs that are 25–30 amino acids in length (FIG. 3C). These domains, named for the presence of a tandem pair of isoleucine and glutamine residues (Cheney, R. E. et al., 1992, Curr. Opin. Cell Biol. 4:27–35), are present in a number of proteins including myosin heavy chain, several unconventional myosins, and the neural protein neuromodulin, also known as GAP43 (Cheney et al., supra; Espreafico, E. M. et al., 1992, J. Cell Biol. 119:1541–1557; Brockerhoff, S. E. et al., 1994, J. Cell Biol. 124:315–323; Alexander, K. A. et al., 1988, J. Biol. Chem. 263:7544–7549).

IQ motifs in these proteins mediate calcium-independent binding to calmodulin and calmodulin-related proteins. As calmodulin is a primary regulator of calcium-dependent cellular processes, its potential association with IQGAP1 might serve to link ras signals to some calcium-regulated pathway. As shown in FIG. 3C, the first of the four IQ motifs in IQGAP1 is very similar throughout to the conserved IQ motif in myosin heavy chain that is responsible for binding to the essential light chain (ELC, also referred to as the alkali light chain), a structural relative of calmodulin that represents one of two myosin-associated light chains. The typical hexameric myosin molecule from muscle or non-muscle tissue consists of two heavy chains complexed with two molecules each of a regulatory light chain and an ELC (Emerson, C. P. and Bernstein, S. I., 1987, Ann. Rev. Biochem. 56:695–726). Although the ELC is structurally related to calmodulin, it does not bind calcium, and its role in myosin function has remained elusive. The presence of a putative binding site in IQGAP1 for the ELC suggests that IQGAP1 may be modulated in part by interaction with the ELC. Alternatively, an interaction between IQGAP1 and ELC might affect myosin function, possibly via a competetion by IQGAP1 and ELC for the same binding site on myosin.

N-terminal repeats

The IQGAP1 protein sequence also contains six copies of a novel 50–60 amino acid motif with the consensus sequence indicated in FIG. 3D. Using the ProfileSearch program (GCG/Wisconsin) to search the SwissProt database, no matches to the consensus sequence shown in FIG. 3D were found. Neither the unique N-terminal repeats nor the IQ motifs occur in the region of similarity to sar1 (FIG. 3A). No other protein motifs that are typically found in signalling proteins, such as SH2, SH3, or pleckstrin-homology domains, are apparent in the IQGAP1 protein.

Recombinant IOGAP1

Recombinant IQGAP1 or any fragment thereof (e.g., a biologically active domain) can be expressed using known methods. DNA sequences encoding IQGAP1 can be cloned into commercially available expression vectors and expressed in E. coli.

For example, the maltose binding protein fusion and purification system (New England Biolabs) can be used to overexpress the IQGAP1 fusion protein. The IQGAP1 gene can be inserted downstream and in frame of the gene encoding maltose binding protein (malE). In the absence of convenient restriction sites, PCR can be used in order to appropriately modify the cDNA sequence. This well known method can facilitate construction of the recombinant plasmid. Immediately upstream of the insertion site of the pMalE plasmid is region encoding a factor Xa cleavage site. The presence of this specific proteolytic-sensitive site allows liberation of the cloned protein from the maltose binding protein without additional amino acids attached at the N-terminus, an advantage over other methods for expressing and purifying recombinant proteins in bacteria. Using this expression system, the recombinant protein can be targeted to either the cytoplasm or periplasmic space, depending upon the presence or absence of the male signal sequence. Purification of the fusion protein can be achieved by passing the crude cell lysate over an amylose resin column, to which the male fusion protein specifically binds. The eluted pure hybrid protein can then be cleaved by factor Xa and the protein of interest purified from maltose binding protein and factor Xa by standard column chromatography.

Other expression systems, e.g., the glutathione-S-transferase gene fusion system (Pharmacia), may also be used to express all or part of the IQGAP1 protein (see FIG. 5). In this system, IQGAP1 DNA sequences are cloned into the GEX-2 vector, and fusion proteins expressed in E. coli. Purification of the resulting recombinant proteins is accomplished by standard column chromatography using glutathione Sepharose 4B beads.

Alternatively, IQGAP1 can be expressed using a eucaryotic expression system. Expression vectors and eurcaryotic cells suitable for expressing recombinant proteins (e.g., mammalian cells, insect cells, yeast cells) are also well known in the art.

Antibody Production and Western Blotting

In order to identify the IQGAP1 polypeptide in cellular extracts and study its potential association with other molecules, such as ras or related members of the ras family of GTPases, antibodies which specifically bind to IQGAP1 are useful. Synthetic peptides designed from the predicted IQGAP1 sequence and/or the purified polypeptide produced by bacterial or eucaryotic cells can be used as antigens to immunize animals for the production of polyclonal antisera using standard protocols.

Antibodies directed against specific antigens may be detected by any of several methods known to those skilled in the art, e.g., by using an Ouchterlony double diffusion assay or an enzyme-linked immunoabsorbent assay (ELISA). In double diffusion assays, antigen and antibodies are placed in separate wells cut in a matrix, e.g., agarose on the surface of a glass plate. The contents of both wells diffuse through the matrix in all directions. Where the diffusing antigen and antigen-specific antibodies meet, a precipitin line forms. ELISA involves coating a substrate, e.g., well in a plastic dish, with a purified antigen. Serum to be tested is then added to the well. If present, antigen specific antibodies attach to the antigen coating the well. Non-binding material is washed away and a marker enzyme e.g., horse radish peroxidase or alkaline phosphatase, coupled to a second antibody directed against the antigen-specific primary antibody is added in excess and the non-adherent material is washed away. Finally the enzyme substrate is added to the well and the enzyme catalyzed conversion is monitored as indicative of presence of the antigen.

To produce monoclonal antibodies, antibody-producing cells from the challenged animal can be immortalized (e.g., by fusion with an immortalizing fusion partner) to produce monoclonal antibodies. Monoclonal antibody-producing hybridomas can then be screened for antibody binding to the IQGAP1 polypeptide as described above.

The invention can employ not only intact monoclonal or polyclonal antibodies, but also an immunologically-active antibody fragment, for example, a Fab or (Fab)$_2$ fragment; an antibody heavy chain, an antibody light chain; a genetically engineered single-chain Fv molecule (Ladner et al., U.S. Pat. No. 4,946,778); or a chimeric antibody, for example, an antibody which contains the binding specificity of a murine antibody, but in which the remaining portions are of human origin.

The IQGAP1-specific antibodies can be employed in Western analyses in order to identify recombinant clones expressing the IQGAP1 gene product.

Diagnostic Uses

For diagnostic purposes, IQGAP1 antibodies can be used in Western blotting assays to detect neoplastic cells based on the specific binding of antibodies to the IQGAP1 gene product. A decrease in IQGAP1 may indicate a neoplasm or pre-cancerous state.

Cell lysates can be prepared from cultured cells or tissue biopsied from a patient. For example, monolayers of cultured cells can be scraped from the plates and solubilized in detergent-containing lysis buffer. The cell extract as well as purified IQGAP1 polypeptide (as a positive control) can then separated by SDS-polyacrylamide gel electrophoresis, followed by transfer to nitrocellulose by electroblotting. To immunologically detect the IQGAP1 polypeptide on the Western blot, a typical antibody binding procedure can be employed, using an alkaline phosphatase-based detection protocol, as described above. Pre-immune serum can be used as an important control for non-specific reactions. The Northern and Western blotting assays can be used in tandem to confirm expression of IQGAP1 in a given biological sample.

Individuals at risk for developing cancer can also be screened for genetic lesions in IQGAP1 DNA using Southern blotting techniques. Specifically, detection of a DNA translocation involving the IQGAP1 gene may be used to diagnose certain tumors.

Measuring the level of expression of IQGAP1 RNA can be accomplished using Northern blot analyses in which IQGAP1 specific RNA is detected by its binding to labeled IQGAP1-specific DNA probes. Alternatively, IQGAP1 transcripts can be amplified using RNA-PCR with IQGAP1 specific probes. Southern and Northern blotting techniques as well as PCR methods are well known to those skilled in the art.

Therapeutic uses

Ras oncogenes have been shown to be present in 5 to 40% of human tumors, including cancers of the bladder, breast, colon, kidney, lung, ovary, pancreas, and stomach as well as melanomas, teratocarcinomas, neuroblastomas, gliomas and tumors of hematopoietic and lymphoid origin.

Constitutive activation is the hallmark of oncogenic ras in human tumors. Overexpression of the normal ras gene product which can result in an abnormal level of enzymatic activity may also contribute to carcinogenesis. The invention can be used to decrease ras activity and thus, treat tumors characterized by aberrant ras expression.

Peptide therapy

For the treatment of patients afflicted with this class of tumors, the invention can be used to downregulate or decrease the activity of p21$^{ras}$. The purified IQGAP1 polypeptides can be administered in a pharmaceutically acceptable carrier, e.g., physiological saline.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into polypeptides, are well known in the art. Similarly, the replacement of an L-amino acid residue is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged amino- and carboxy-termini of the peptides would have the additional benefit of enhancing passage of the peptide through the hydrophobic cellular membrane and into the cell.

The polypeptides can be administered intraperitoneally, intramuscularly, subcutaneously, or intravenously.

Standard methods for intracellular delivery of peptides can be used, e.g. with liposomes. Such methods are well known to those of ordinary skill in the art. It is expected that an intravenous dosage of approximately 1 to 100 μmoles of the peptide of the invention would be administered per kg of body weight per day.

Gene therapy

In some cases, patients may be treated by administering the nucleic acid of the invention, such that the expression of recombinant polypeptide takes place in the cells, e.g., tumor cells, of the patient, such as tumor cells. The nucleic acid of the invention may be introduced into target cells of a patient by standard vectors and/or gene delivery systems. Suitable gene delivery systems include liposomes, receptor-mediated delivery systems, naked DNA, and viral vectors such as herpes viruses, retroviruses, and adenoviruses, among others.

For treatment of cancer, a therapeutically effective amount of a nucleic acid administered in a pharmaceutically acceptable carrier to reduce the activity of oncogenic p21$^{ras}$. A pharmaceutically acceptable carrier is a vehicle that is suitable, i.e., biologically compatible, for administration to an animal, e.g. physiological saline. A therapeutically effective amount is an amount of the nucleic acid of the invention which is capable of producing a medically desirable result in a treated animal.

As is well known in the medical arts, dosages for any one patient depends upon many factors, including the patient's size, body surface area, age, the particular compound to be administered, sex, time and route of administration, general health, and other drugs being administered concurrently. Dosages for the nucleic acid molecules of the invention will vary, but a preferred dosage for intravenous administration is approximately from $10^6$ to $10^{22}$ copies of the nucleic acid molecule.

Once improvement of the patient's condition has occurred, a maintenance dose may be administered, if necessary. Subsequently, the dosage or the frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

Other embodiments

Also included in the invention are analogues of the native IQGAP1 protein or polypeptides. Analogs can differ from the native peptides of IQGAP1 by amino acid sequence, or by modifications which do not affect the sequence, or by both.

Preferred analogs include peptides whose sequences differ from the wild-type sequence (i.e., the sequence of the homologous portion of the naturally occurring peptide) only by conservative amino acid substitutions, preferably by only one, two, or three, substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. Table 1 lists a number of conservative amino acid substitutions.

Modifications (which do not normally alter primary sequence) include in vivo or in vitro chemical derivitization of polypeptides, e.g., acetylation or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation e.g., mammalian glycosylating or deglycosylating enzymes. Also included are sequences which have phosphorylated amino acid residues, e.g., phosphotyrosine, phosphoserine, or phosphothreonine For treatment of localized tumors, a bio-polymer delivery system designed for the slow release of the polypeptide of the invention may be implanted in close proximity to the tumor mass. Such bio-polymer delivery systems are well known in the art (see, e.g., Folkman et al., U.S. Pat. No. 4,164,560, herein incorporated by reference).

TABLE 1

CONSERVATIVE AMINO ACID REPLACEMENTS

| For Amino Acid | Code | Replace With |
|---|---|---|
| Alanine | A | D-Ala, Gly, Aib, β-Ala, Acp, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, Aib, β-Ala, Acp |
| Isoleucine | I | D-Ile, Val, D-Val, AdaA, AdaG, Leu, D-Leu, Met, D-Met |
| Leucine | L | D-Leu, Val, D-Val, AdaA, AdaG, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Proline | P | D-Pro, L-I-thioazolidine-4-carboxylic acid, D-or L-1-oxazolidine-4-carboxylic acid (Kauer, U.S. Pat. No. (4,511,390) |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met, AdaA, AdaG |

Other embodiments are within the following claims.

What is claimed is:

1. A substantially pure nucleic acid comprising a sequence encoding human IQGAP1.

2. The nucleic acid of claim 1, wherein said nucleic acid comprises the sequence of SEQ ID NO:2.

3. A substantially pure nucleic acid comprising a sequence which hybridizes at high stringency to the nucleic acid of claim 1.

4. The substantially pure preparation of nucleic acid of claim 1, wherein said sequence encodes a product which comprises the amino acid sequence given in SEQ ID NO: 1.

5. A cell comprising the nucleic acid of claim 1.

6. The cell of claim 5, wherein said cell expresses said nucleic acid.

7. A substantially pure nucleic acid wherein said nucleic acid hybridizes at high stringency to the nucleic acid of claim 2.

8. The substantially pure preparation of nucleic acid of claim 2 and degenerate variants thereof, wherein said sequence encodes a product which comprises the amino acid sequence given in SEQ ID NO: 1.

* * * * *